US012174158B2

(12) United States Patent
Azizi et al.

(10) Patent No.: US 12,174,158 B2
(45) Date of Patent: *Dec. 24, 2024

(54) FAST IN-FIELD CHROMATOGRAPHY SYSTEM AND METHOD USING ISOTOPE MEASUREMENTS

(71) Applicant: Baker Hughes Oilfield Operations LLC, Houston, TX (US)

(72) Inventors: Salar Azizi, Hannover (DE); Bastian Baecker, Falkensee (DE); Ansgar Cartellieri, Celle (DE)

(73) Assignee: Baker Hughes Oilfield Operations LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/132,236

(22) Filed: Apr. 7, 2023

(65) Prior Publication Data

US 2023/0243784 A1 Aug. 3, 2023

Related U.S. Application Data

(63) Continuation of application No. 17/227,874, filed on Apr. 12, 2021, now Pat. No. 11,624,733.

(51) Int. Cl.
  *G01N 30/20* (2006.01)
  *G01N 30/02* (2006.01)
  *G01N 30/06* (2006.01)

(52) U.S. Cl.
  CPC .............. *G01N 30/20* (2013.01); *G01N 30/06* (2013.01); *G01N 2030/025* (2013.01)

(58) Field of Classification Search
  None
  See application file for complete search history.

(56) References Cited

U.S. PATENT DOCUMENTS

| 4,887,464 | A | 12/1989 | Tannenbaum |
| 7,124,030 | B2 | 10/2006 | Ellis |
| 7,174,254 | B2 | 2/2007 | Ellis |
| 8,536,524 | B2* | 9/2013 | Pomerantz ............ E21B 49/005 |
| | | | 250/281 |
| 10,215,737 | B2* | 2/2019 | Coleman ................ G01N 30/74 |
| 2004/0014223 | A1 | 1/2004 | Audibert |

(Continued)

FOREIGN PATENT DOCUMENTS

EP   1508794   2/2005

OTHER PUBLICATIONS

International Search Report and Written Opinion mailed Jun. 25, 2022 in corresponding PCT Appln. No. PCT/US22/24261.

*Primary Examiner* — Kristina M Deherrera
*Assistant Examiner* — Gedeon M Kidanu
(74) *Attorney, Agent, or Firm* — Hogan Lovells US LLP

(57) ABSTRACT

A system for separation of components of a natural gas product uses a first separation column to receive the natural gas product and to provide first stage components including a first component gas, uses a gas converter to provide second stage components that includes third component gas from at least a second component gas of such first stage components, and uses a second separation column to provide third stage components that includes the first component gas, the third component gas, and one or more additional carbon-based components provided in or over a period of time associated with the separation of the components of the natural gas product.

20 Claims, 15 Drawing Sheets

(56) References Cited

U.S. PATENT DOCUMENTS

| | | |
|---|---|---|
| 2005/0082473 A1 | 4/2005 | Socki |
| 2006/0198780 A1* | 9/2006 | Ota ........................ B01D 53/62 |
| | | 423/418.2 |
| 2014/0208797 A1 | 7/2014 | Kelley |
| 2014/0332201 A1 | 11/2014 | Castrogiovanni |
| 2015/0345258 A1 | 12/2015 | Sanborn |
| 2016/0265725 A1 | 9/2016 | Lachance |
| 2016/0356759 A1 | 12/2016 | Calleri |
| 2021/0001267 A1 | 1/2021 | Novek |

* cited by examiner

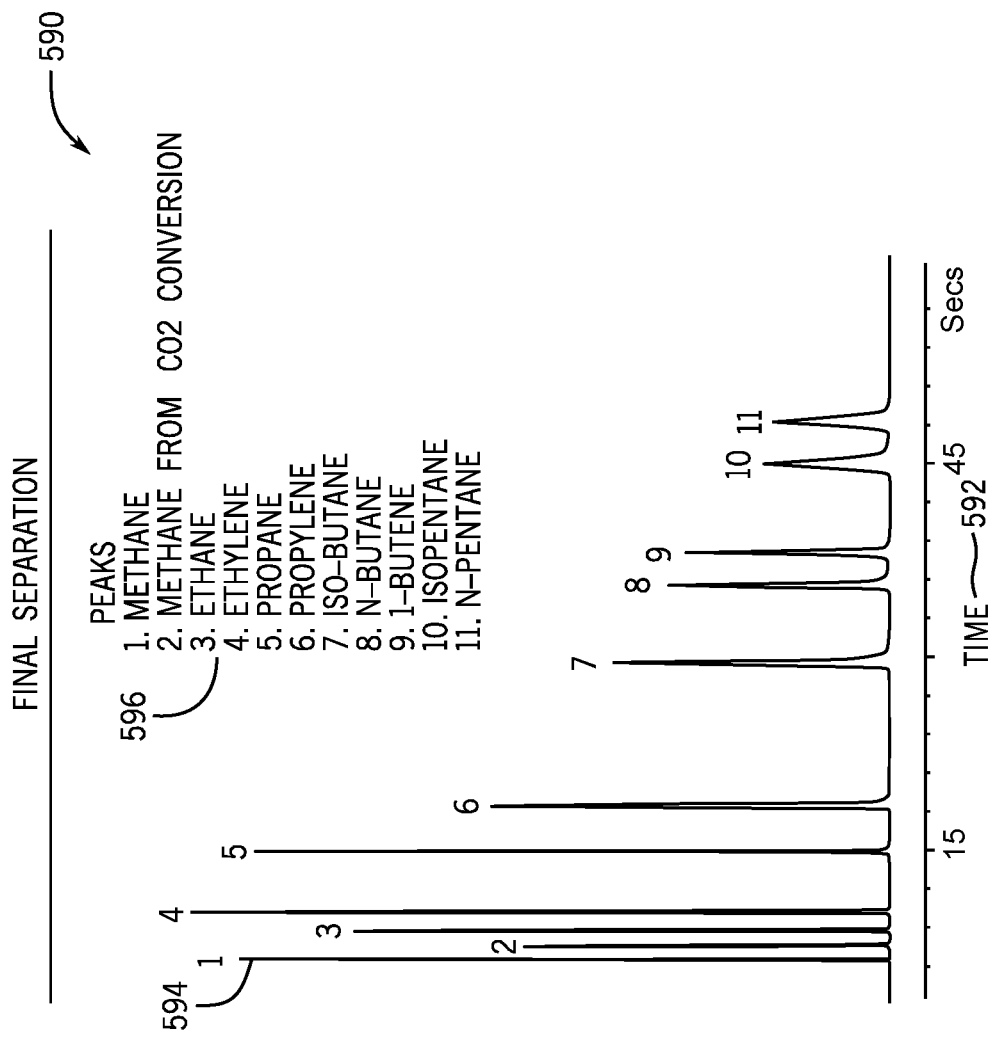

FAST IN-FIELD CHROMATOGRAPHY SYSTEM AND METHOD USING ISOTOPE MEASUREMENTS

CROSS-REFERENCE(S) TO RELATED APPLICATION(S)

This application is a continuation of U.S. patent application Ser. No. 17/227,874, filed Apr. 12, 2021, titled FAST IN-FIELD CHROMATOGRAPHY SYSTEM AND METHOD USING ISOTOPE MEASUREMENTS, now U.S. Pat. No. 11,624,733 issued Apr. 11, 2023, the disclosure of which is incorporated by reference herein for all intents and purposes.

BACKGROUND

1. Field of Invention

This invention relates in general to equipment used in the natural gas industry, and in particular, to fast in-field chromatography of natural gas products.

2. Description of the Prior Art

A drilling well is a structure formed in subterranean or underwater geologic structures, or layers. Such subterranean or underwater geologic structures or layers incorporate pressure that may be further enhanced by supplementing formation fluids (such as liquids, gasses or a combination) into a drill site or a well site (such as a wellbore). Chromatography may be performed in a lab setting for natural gas product samples gathered from a well or drill site. Chromatography may be performed using a serial or a parallel separation column that may take as much as 3 to 10 minutes to determine various components in a natural gas product sample. Certain chromatography systems may be able to separate certain hydrocarbon components, such as C1 (methane) to C5 (pentane) within a minute, but certain other components that may or may not be hydrocarbons, including carbon dioxide ($CO_2$) and ethane, may not be separated due to overlapping spectral peaks that may not be detected separately in a subsequent spectrometer or other detector.

SUMMARY

In at least one embodiment, a system for separation of components of a natural gas product includes a first separation column, a gas converter, and a second separation column. In at least one embodiment, a first separation column is to receive a natural gas product and to provide first stage components that include at least a first component gas and second component gas. In at least one embodiment, a gas converter is to receive first stage components and to provide second stage components that include the first component gas and a third component gas, the third component gas formed by conversion of the second component gas. In at least one embodiment, a second separation column is to receive second stage components and to provide third stage components. In at least one embodiment, third stage components may include the first component gas, the third component gas, and one or more additional carbon-based components. In at least one embodiment, individual third stage components are provided in or over a period of time associated with separation of components of a natural gas product by such a system.

In at least one embodiment, a method for separation of components of a natural gas product includes receiving a natural gas product in a first separation column. In at least one embodiment, such a method includes receiving, in the gas converter, first stage components that includes at least a first component gas and a second component gas, from a first separation column. In at least one embodiment, such a method includes a further step of receiving, from the gas converter to a second separation column, second stage components including the first component gas and a third component gas, the third component gas formed by conversion of the second component gas. In at least one embodiment, from such a second separation column, a method so described includes providing third stage components. In at least one embodiment, such third stage components include the first component gas, the third component gas, and one or more additional carbon-based components. In at least one embodiment, individual third stage components are provided in or over a period of time associated with separation of such components of a natural gas product.

In at least one embodiment, a method for separation of components of a natural gas product includes determining calibration points associated with a combustion chamber of a chromatography system. In at least one embodiment, such a method includes associating a first separation column with a gas converter and a second separation column. In at least one embodiment, such a method includes determining that a natural gas product is available for sampling, such as by providing a natural gas product with a carrier gas to a first separation column. In at least one embodiment, still further, a method for a fast in-field chromatography system includes enabling a spectrometer or detector to provide spectral peaks at different times based in part on components separated in one or more of a first separation column, a gas converter, and a second separation column of a fast in-field chromatography system.

BRIEF DESCRIPTION OF THE DRAWINGS

Various embodiments in accordance with the present disclosure will be described with reference to the drawings, in which:

FIGS. 5B-D illustrate results from a system for separation of components of a natural gas product, such as described in FIG. 5A, of at least one embodiment herein;

DETAILED DESCRIPTION

Figure 1:
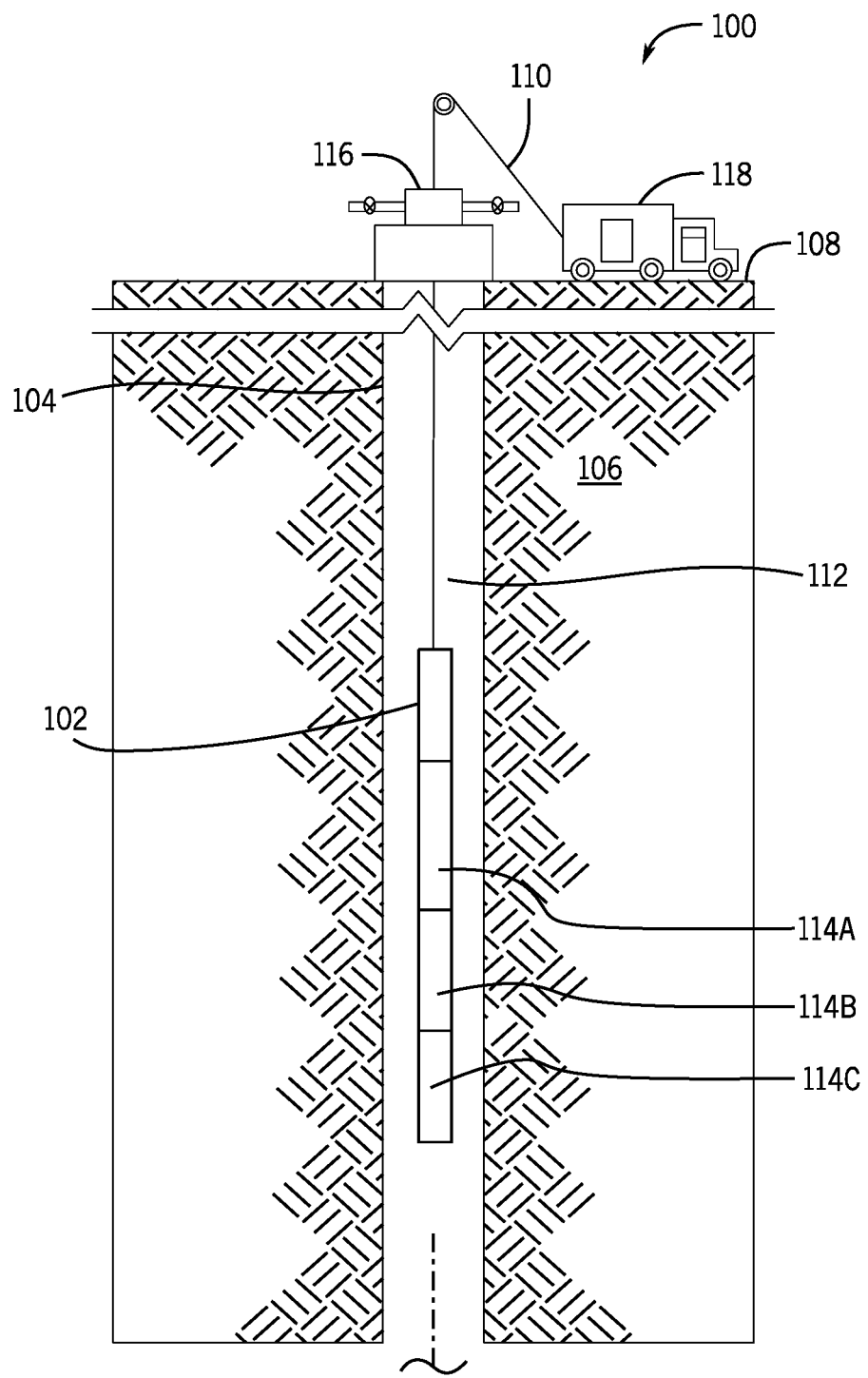
FIG. 1 illustrates an example environment subject to improvements of at least one embodiment herein.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Various other functions can be implemented within the various embodiments as well as discussed and suggested elsewhere herein. In at least an aspect, the present disclosure is to a system and a method for separation of components of a natural gas product.

In at least one embodiment, a system and a method for separation of components of a natural gas product is able to determine, from different carbon isotopes, as to one or more carbon-based components in a natural gas product. Element carbon has two stable isotopes (such as, $^{12}C$ and $^{13}C$). In at least one embodiment, isotopes in a natural gas molecule may vary according to how such a molecule may be formed (such as by biogenic and thermogenic processes). In at least one embodiment, carbon isotope ratios ($^{12}C/^{13}C$) may be used for various natural gas studies, including for petroleum, source rock typing and identification, reservoir compartmentalization, formation pressure identification, reservoir seal effectiveness, and migration pathways. As such, demand on carbon isotope ratio analysis has increased for oil and gas markets, and in particular for mud-gas logging services. In at least one embodiment, gas separation herein has an applied isotope ratio measurement techniques to improve a cycle time for measurements of isotope ratios for C1 (methane) to C5 (pentane) and for CO2 to one (1) minute.

In at least one embodiment, a cycle time for isotope ratio measurement in an online mud-gas stream that can be improved to approximately 1 minute in a fast in-field chromatography system and method herein. In at least one embodiment, speeding up gas separation is a step that enables faster carbon isotope ratio measurements. In at least one embodiment, such a method and system address an issue in a measurement cycle time for carbon isotope ratios that is done in an online mud-gas stream which was previously slow (such as, around few minutes).

In at least one embodiment, such a method and system use an intermediate reaction step to convert $CO_2$ in a natural gas product sample gas to methane, which reduces a later separation effort for $CO_2$ in a natural gas product. In at least one embodiment, such a feature reduces time for separation and may be tracked by two distinct spectral peaks for methane in a spectrometer or detector. In at least one embodiment, a first spectral peak refers to original methane in a natural gas product, such as a gas stream and a second peak refers to converted $CO_2$. In at least one embodiment, each spectral peak may be indicative of a different isotope of methane. In at least one embodiment, all separated spectral peaks are catalytically combusted in a further step. In at least one embodiment, a catalytic combustion module may be used and may include a catalyst that can be regenerated by blowing hot air over it. In at least one embodiment, such a feature reduces maintenance costs in for a fast in-field chromatography system.

In at least one embodiment, a system and method herein are faster and fitting for fast in-field chromatography without requiring samples to be sent to a laboratory for results. In at least one embodiment, as maintenance time is lower, a system herein is online for considerably longer periods. In at least one embodiment, results for separation of natural gas components may require isotope ratio measurements, including those performed by mass spectrometry coupled to system described herein. In at least one embodiment, a whole system testing and calibration may be asserted to address such mass spectrometry requirements. In at least one embodiment, while parallel and series concept of gas chromatography can be used to speed up gas separation prior to detection step, their cycle times would only be reduced marginally, and still requires a few minutes for separation.

In at least one embodiment, FIG. 1 illustrates an example environment 100 subject to improvements described herein. A fast in-field chromatography system may include one or more downhole and/or platform-based tools 102. In at least one embodiment, a platform-based tool may be above terrain surface 108 (of terrain 106) or above water surface. In at least one embodiment, such a downhole and/or platform-based tool 102 may be part of a string 112 of tools, which may include other components utilized for wellbore operations.

In at least one embodiment, a string 112 may include other tools 114A-114C than components or an entire fast in-field chromatography system. In at least one embodiment, such tools may be part of sensors, measurement devices, communication devices, and the like. In at least one embodiment, a string 112 may include one or more tools to enable at least one of a logging operation (such as mud-gas logging), for perforating operation, or for well intervention. In at least one embodiment, nuclear logging tools, fluid sampling tools, and core sampling devices may be also used in a string 112. In at least one embodiment, perforating operations may include ballistic devices being lowered into a wellbore 104 to perforate casing or the formation. In at least one embodiment, well interventions may include operations relating to analysis of one or more features of a wellbore 104, followed by performing one or more tasks in response to at least one feature. In at least one embodiment, one or more features may include data acquisition, cutting, and cleaning. As such, in at least one embodiment, a string 112 may refer to a combination of one or more tools lowered into a wellbore 104. In at least one embodiment, passive devices may also be included, such as centralizers or stabilizers. In at least one embodiment, tractors may be provided to facilitate movement of a string 112.

In at least one embodiment, power and/or data conducting tools may be used to send and receive signals and/or electrical power. In at least one embodiment, sensors may be incorporated into various components of a string 112 and may be enabled to communicate with a surface (platform) or with other string components. In at least one embodiment, such communication may be via a cable 110, via mud pulse telemetry, via wireless communications, and via wired drill pipe, in a non-limiting manner. In at least one embodiment, it should be appreciated that while embodiments may include a wireline system, a rigid drill pipe, coiled tubing, or any other downhole exploration and production methods may be utilized with at least one embodiment herein.

In at least one embodiment, an environment 100 includes a wellhead assembly 116 shown at an opening of a wellbore 104 to provide pressure control of a wellbore and to allow for passage of equipment into a wellbore 104. In at least one embodiment, such equipment may include a cable 110 and a string 112 of tools. In at least one embodiment, a cable 110 is or may include a wireline that is spooled from a service truck 118. In at least one embodiment, a cable 110 may extend to an end of a string 112. In at least one embodiment, during operation, a cable 110 may be provided with some slack as a string 112 is lowered into a wellbore 104 to a predetermined depth.

In at least one embodiment, fluid may be delivered into a wellbore 104 to drive or assist in movement of a string 112. In at least one embodiment, this may be a case where gravity may not be sufficient to assist, such as in a deviated wellbore. In at least one embodiment, a fluid pumping system may be provided at a surface 108 to pump fluid from a source into a wellbore 104 via a supply line or conduit. In at least one embodiment, control of a rate of travel of a downhole assembly and/or control of tension on a wireline 110 may be provided by a winch on a surface 108. In at least one embodiment, such a winch system may be part of a service tuck 118. In at least one embodiment, a combination of fluid flow rate and tension on a wireline 110 can contribute to a travel rate or rate of penetration of a string 112 into a wellbore 104.

In at least one embodiment, a provided cable 110 may be an armored cable that includes conductors for supplying electrical energy (power) to downhole devices and communication links for providing two-way communication between a downhole tool and surface devices. In at least one embodiment, tools such as tractors, may be disposed along a string 112 to facilitate movement of such a string 112 into a wellbore 104. In at least one embodiment, a string 112 may be retrieved from a wellbore 104 by reeling a provided cable 110 upwards using such a service truck 118. In at least one embodiment, logging operations may be performed as a string 112 is brought to a surface 108.

Figure 2A:
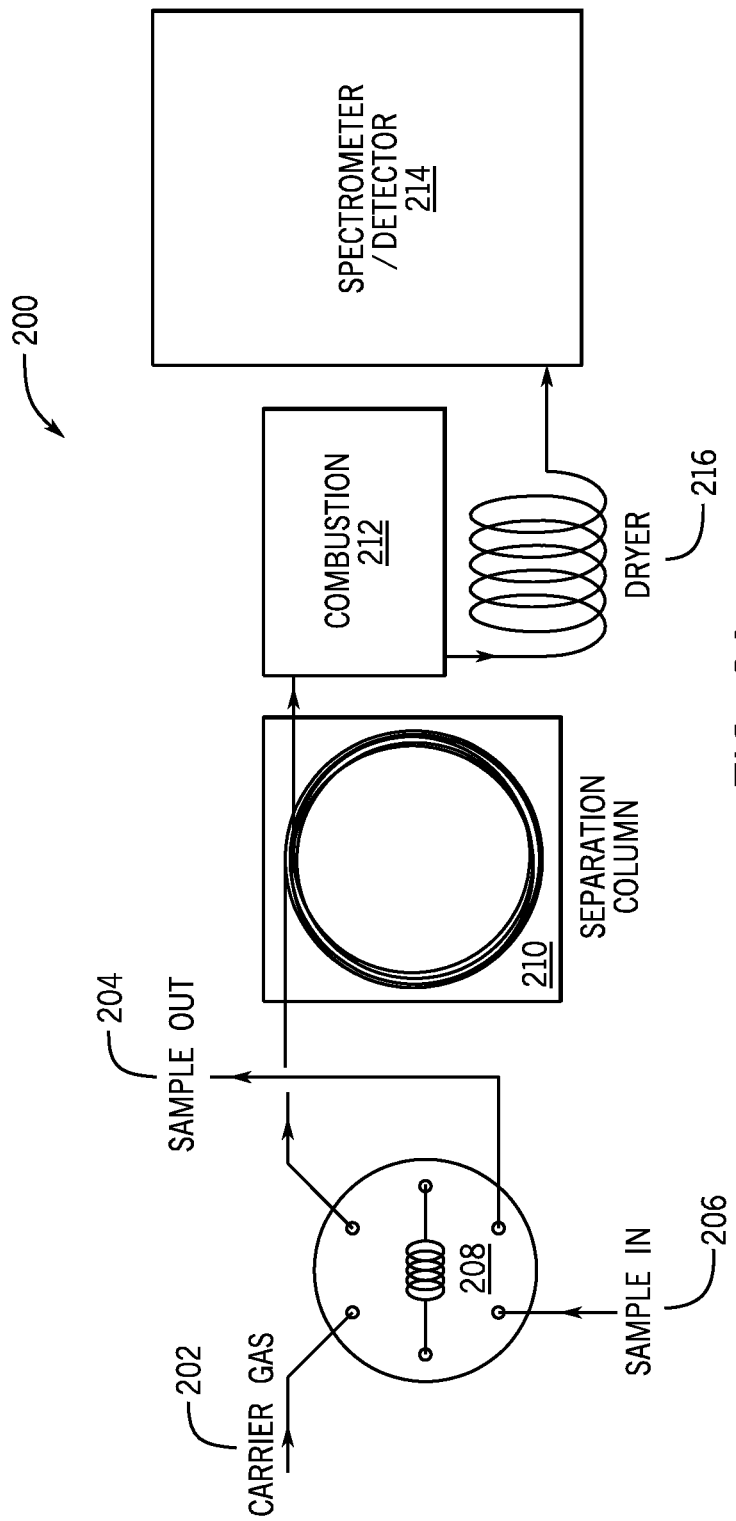
FIG. 2A illustrates a prior art system for separation of components of a natural gas product that is subject to improvements of at least one embodiment herein.

FIG. 2A illustrates a prior art system 200 for separation of components of a natural gas product that is subject to improvements of at least one embodiment herein. Although carbon has two stable isotopes $^{12}C$ and $^{13}C$, an abundance of isotopes in a natural gas molecule varies according to how such a molecule was formed (such as by biogenic and thermogenic processes). Isotope ratios ($^{12}C/^{13}C$) may be used for various natural gas studies. Most developed techniques for carbon isotope ratio measurements of natural gas mixtures may be based on three steps. In at least one embodiment, such three steps may include separation of components, oxidation of components, and a combination of drying and detection. Oxidation of components may result in $CO_2$ formation.

A gas chromatography may be used to separate components of a natural gas product. A carrier gas 202 is provided with a natural gas product 206 into a combination chamber 208. In at least one embodiment, such a combination chamber may include one or more sample loops, one or more pre-columns, and one or more multi-stage valves. A carrier gas may be hydrogen or helium. A natural gas product 206 may be a sample for separation and may be output 204 from a provided vent. Separation of components may occur in a separation column 210 having a coil therethrough. Separation of components may be a limiting step to increase cycle time associated with measurement of such components. A catalytic combustion, via a combustion chamber 212, of separated components converts each natural gas component, which may elute at known retention times, to molecules distinct for each hydrocarbon component in addition to a $CO_2$ component.

Water vapor may be produced during such reaction and may be readily removed by utilizing in a tube dryer 216, such as Nafion®. For isotope ratio measurement, masses 44 ($^{12}C^{16}O_2$) and 45 ($^{13}C^{16}O_2$ & $^{12}C^{16}O^{17}O$) as well as 46 ($^{12}C^{16}O^{18}O$) are determined by detector systems, such as by using mass spectrometry, using cavity ring down spectroscopy, or by using infrared spectroscopy, respectively, and which may be represented in a spectrometer/detector chamber 214.

Figure 2B:
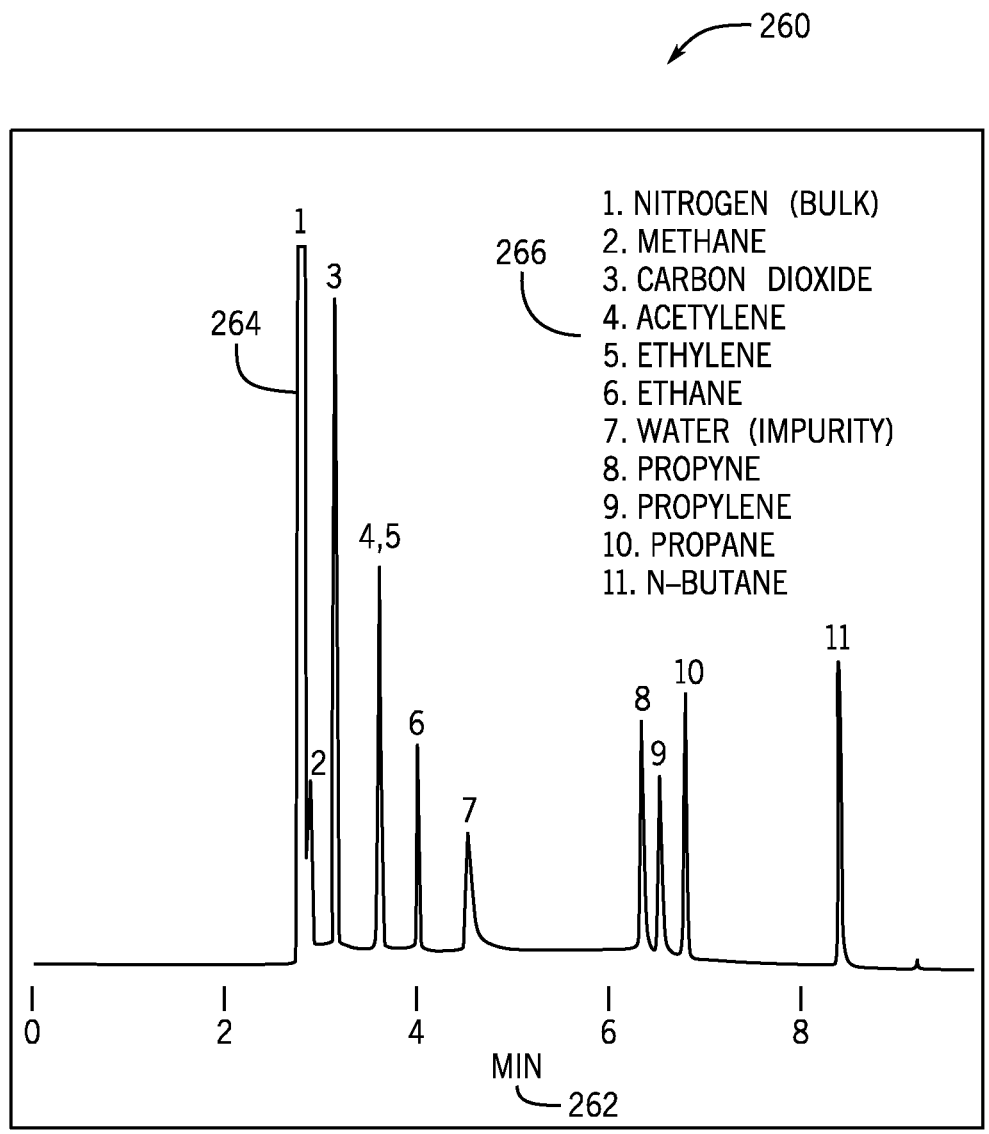
FIGS. 2B-D illustrate results from a prior art system for separation of components of a natural gas product, such as described in FIG. 2A and that is subject to improvements of at least one embodiment herein.
Figure 2C:
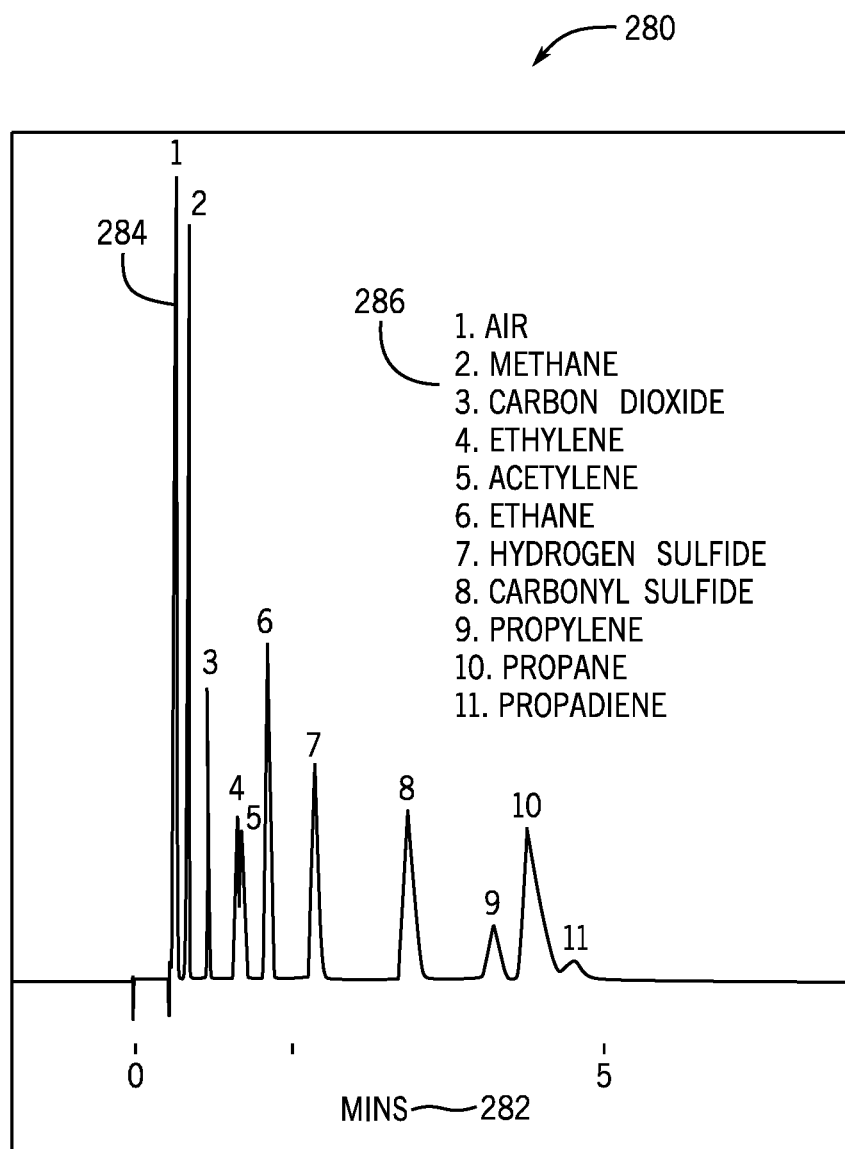
Figure 2D:
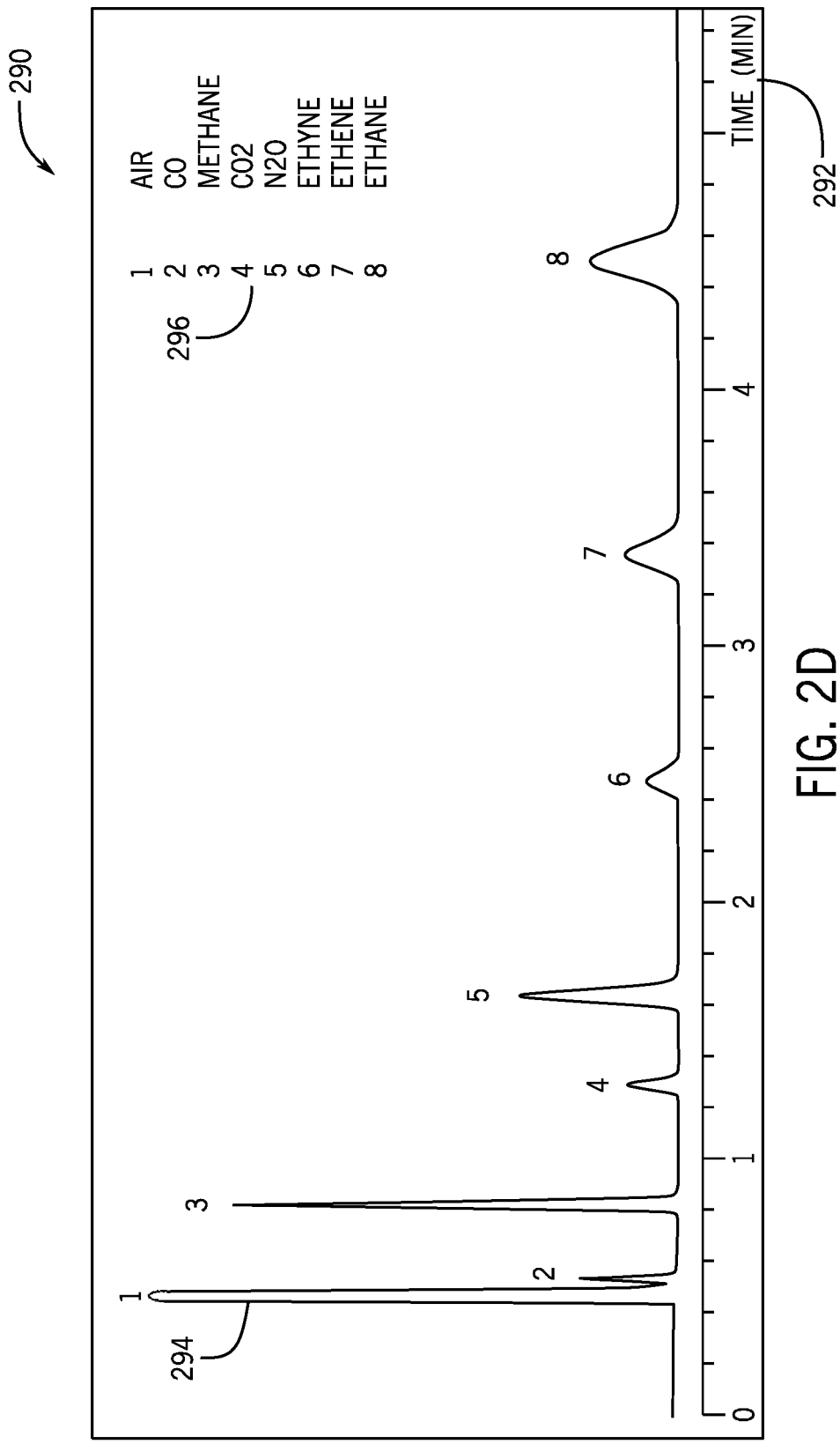

FIGS. 2B-D illustrate results from a prior art system for separation of components of a natural gas product, such as described in FIG. 2A and that is subject to improvements of at least one embodiment herein. FIG. 2B represents a Supel-Q™ PLOT 260 from Supelco®, FIG. 2C represents a HayeSep Q™ plot 280 from VICI®; and FIG. 2D represents a ShinCarbon™ plot 290 from Restek®. A measurement cycle time may be limited to elution velocity of components in a separation column 210. Elution velocity of components may be dependent on temperature and pressure in a separation column 210. Increasing a temperature and a pressure may cause increase of elution velocity, while separation of components may decrease. Optimization of separation resolution and of measurement cycle time are improvements to gas chromatography systems offered by a system and a method for fast in-field chromatography, discussed herein. Separation of natural gas components and of $CO_2$ may be time consuming in such a singular separation column 210.

FIGS. 2B-D represent such time-consuming results 260, 280, 290 from chromatographs of a separation column 210 used in a known gas chromatography system. Such cycle times are demonstrated at above a few minutes in most cases. In FIG. 2B, natural gas component spectral peaks 264 are illustrated with a label 266, for each spectral peak, for a system 200 in FIG. 2A. As illustrated, detection of a final natural gas component, n-butane (label 11) occurs post-8 minutes, illustrated on a minute scale 262 of plot 260. In FIG. 2C, natural gas component spectral peaks 284 are illustrated with a label 286, for each spectral peak, for a system 200 in FIG. 2A. As illustrated, detection of a final natural gas component, propadiene (label 11) occurs at almost a 5-minute mark, illustrated on a minute scale 282 of plot 280. In FIG. 2D, natural gas component spectral peaks 294 are illustrated with a label 296, for each spectral peak, for a system 200 in FIG. 2A. As illustrated, detection of a final natural gas component, ethane (label 8) occurs post-4 minutes, illustrated on a minute scale 292 of plot 290.

Figure 3A:
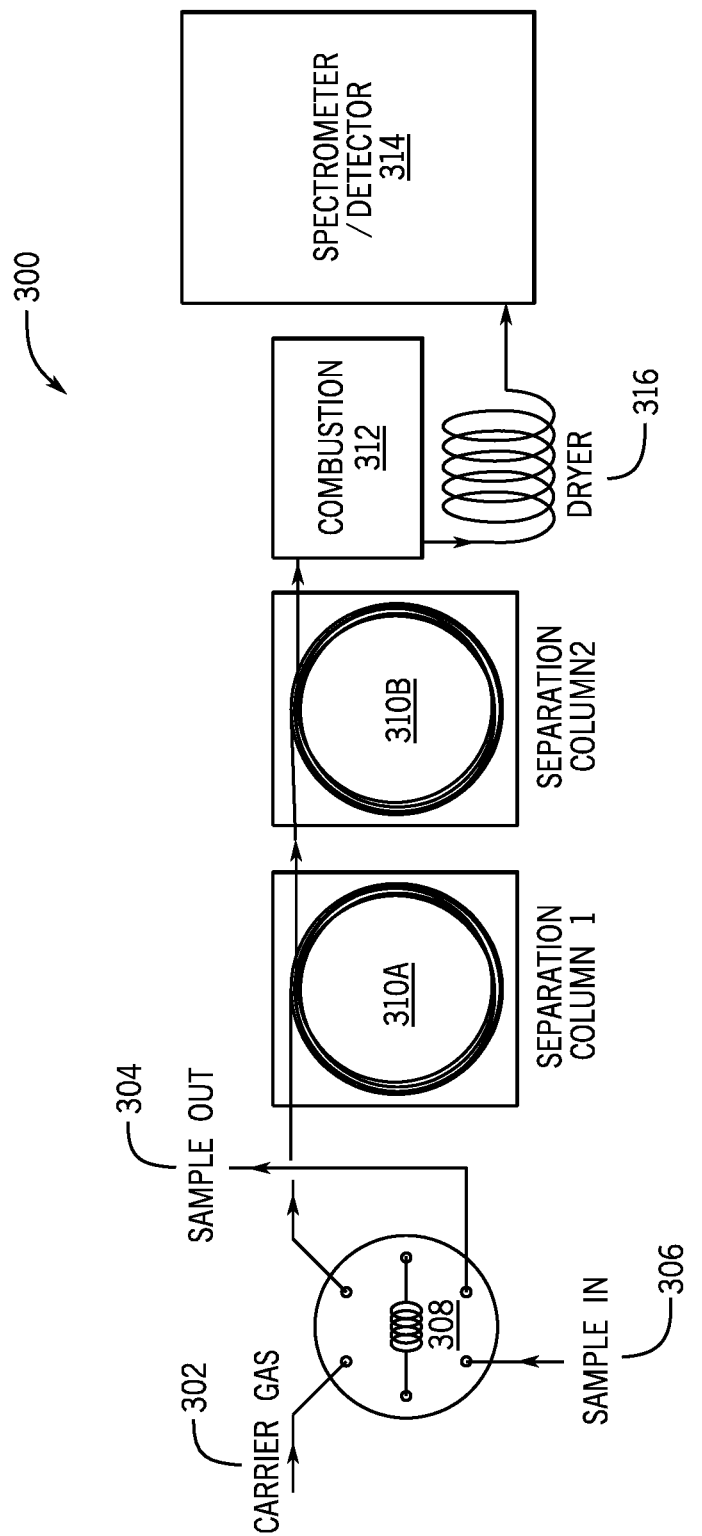
FIG. 3A illustrates a further prior art system for separation of components of a natural gas product that is subject to improvements of at least one embodiment herein.

FIG. 3A illustrates a further prior art system 300 for separation of components of a natural gas product that is subject to improvements of at least one embodiment herein. Such a provided system 200 is a series gas chromatography system. In such a system, separation time of natural gas and $CO_2$ may be reduced by using two different separation columns 310A, 310B. However, such cycle time may be only reduced to a certain time value, which is still at least a few minutes, as illustrated in a provided plot 360 in FIG. 3B. A system 300 of an in-series gas chromatography detector of FIG. 3 includes a combination chamber 308 for a carrier gas 302, for a natural gas product sample 306, and which is let out as a natural gas product sample 304, via a sample outlet. A combustion chamber 312, followed by a dryer 316, and a spectrometer or a detector 314 may be as discussed with respect to a system 200 of FIG. 2A.

Figure 3B:
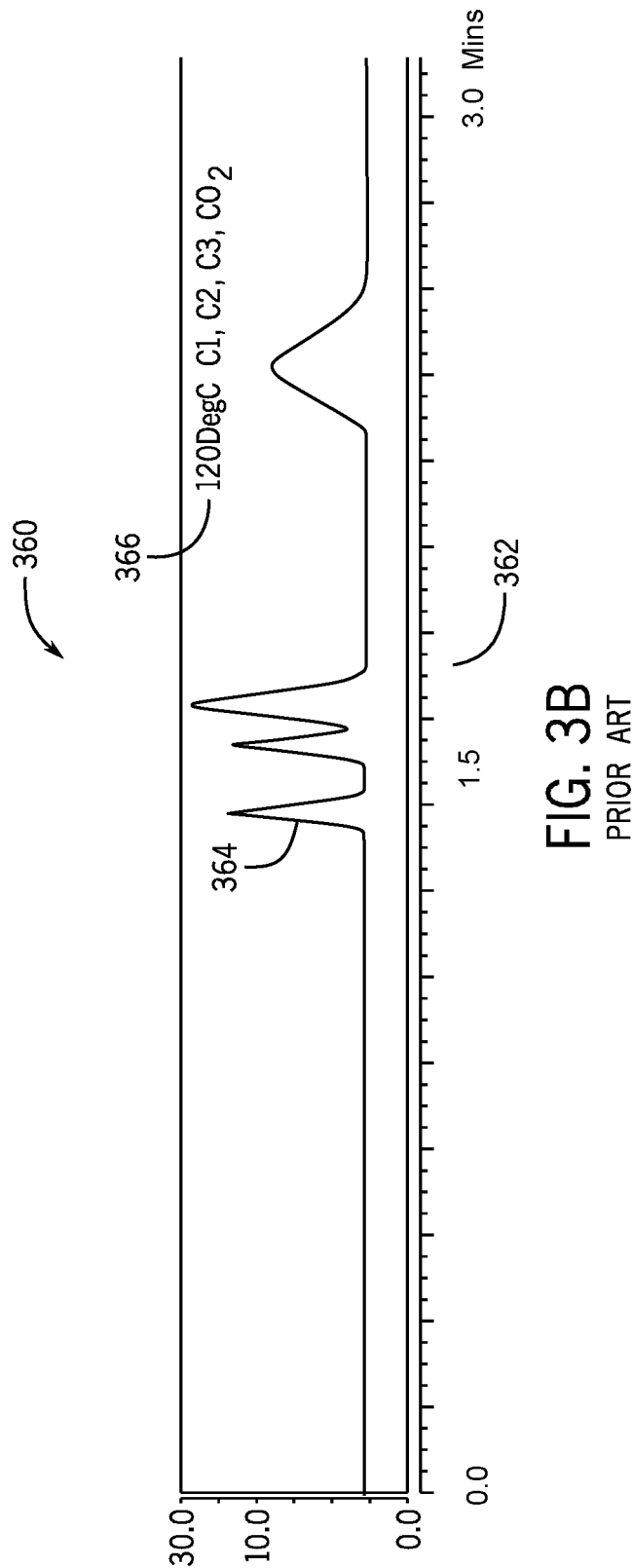
FIG. 3B illustrates results from a prior art system for separation of components of a natural gas product, such as described in FIG. 3A and that is subject to improvements of at least one embodiment herein.

FIG. 3B illustrates results 360 from a prior art system for separation of components of a natural gas product, such as described in FIG. 3A and that is subject to improvements of at least one embodiment herein. A measured chromatograph of C1, C2, C3, and $CO_2$ for a 15-meter silica fused column with a 0.5 meter of HayeSep Q™ column is illustrated in this figure. In FIG. 3B, natural gas component spectral peaks 364 are illustrated with a label 366, for each spectral peak, for a system 300 in FIG. 3A. As illustrated, detection of a final natural gas component, $CO_2$ occurs post-1 minute, illustrated on a minute scale 362 of plot 360. FIG. 3B illustrates a time scale (such as, x-axis having sec/100 measures), which shows that it takes roughly 170 seconds (almost 3 mins) for detection of C1-C3 and of $CO_2$.

Figure 4:
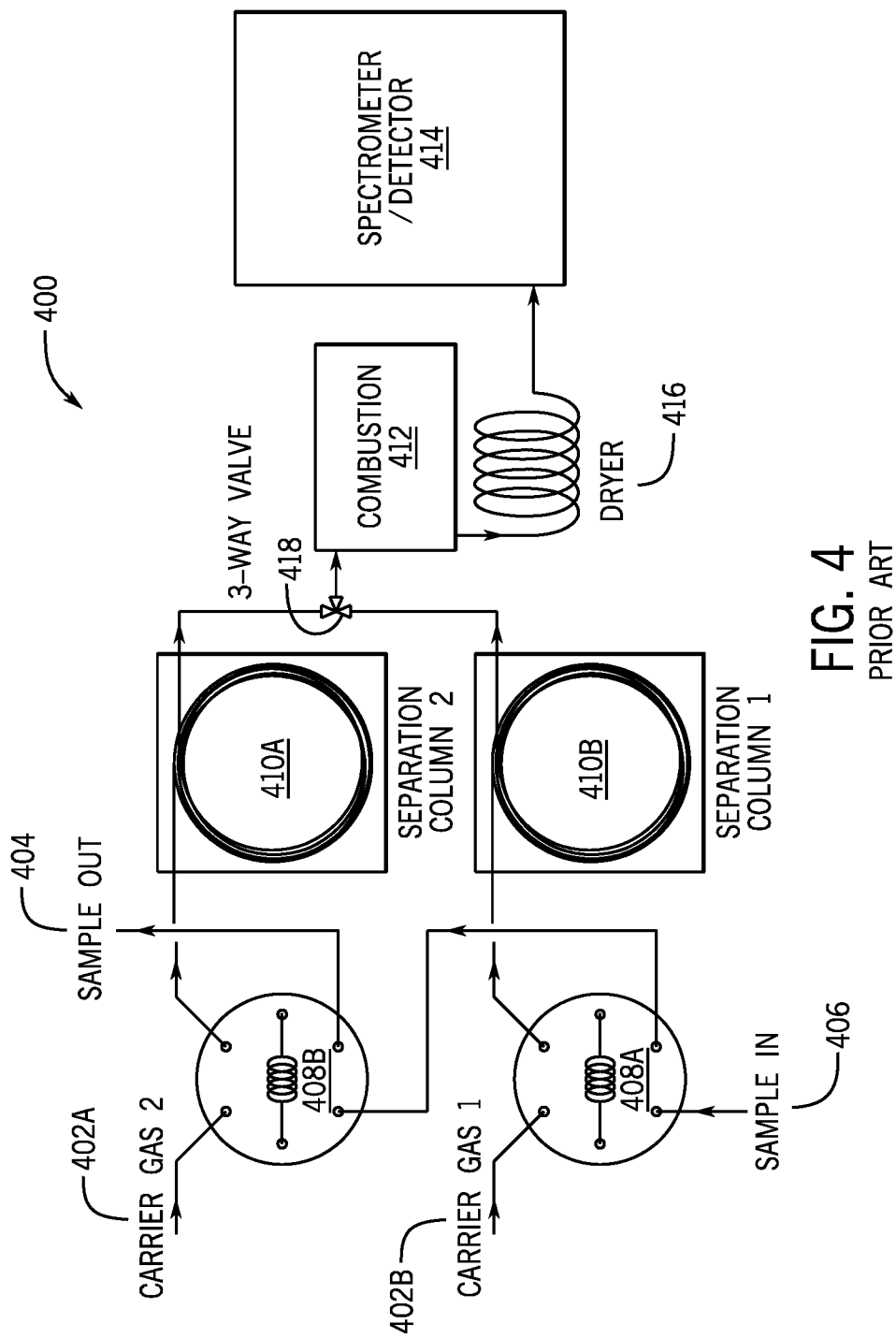
FIG. 4 illustrates yet another prior art system for separation of components of a natural gas product that is subject to improvements of at least one embodiment herein.

FIG. 4 illustrates yet another prior art system 400 for separation of components of a natural gas product that is subject to improvements of at least one embodiment herein. Such a system may be a parallel gas chromatography system. This may be a multiple channel gas chromatograph approach to reduce the cycle time. This may be used for reproducing more data points within a separation time of chromatograph channels. For example, such a system 400 may be equivalent to applying separate chromatograph devices, where sampling starts at a same time but with fewer components being separated in each separation column 410A; 410B, and with remaining components in one or another of these separation columns.

For purposes of economy that may be driven by price and by size of a system, a three-way valve 418 may be used to switch a gas stream between such two separation columns 410A, 410B. This may avoid duplicating combustion chamber 412, dryer 416, and spectrometer/detector 414 components in a system 400. As such, switching time of such a three-way valve 418 may be predefined, based on retention times and on a time window of desired components eluting from each separation column 410A, 410B. A separation temperature and a separation pressure of separation columns 410A, 410B may be also different and well-tuned to prevent overlapping of spectral peaks eluting from different separation columns 410A, 410B.

A system 400 of an in-parallel gas chromatography detector of FIG. 4 incldes separate combination chambers 408A, 408B for different carrier gas 402A, 402B, for a singular natural gas product sample 406, and which is let out as a natural gas product sample 404, via a sample outlet. A combustion chamber 412, followed by a dryer 416, and a spectrometer or a detector 414 may be as discussed with respect to a systems 200, 300 of FIGS. 2A and 3A. A system 400 may be provided, in a similar manner as a system 300, by some mud-gas vendors in an oil and gas sector.

Figure 5A:
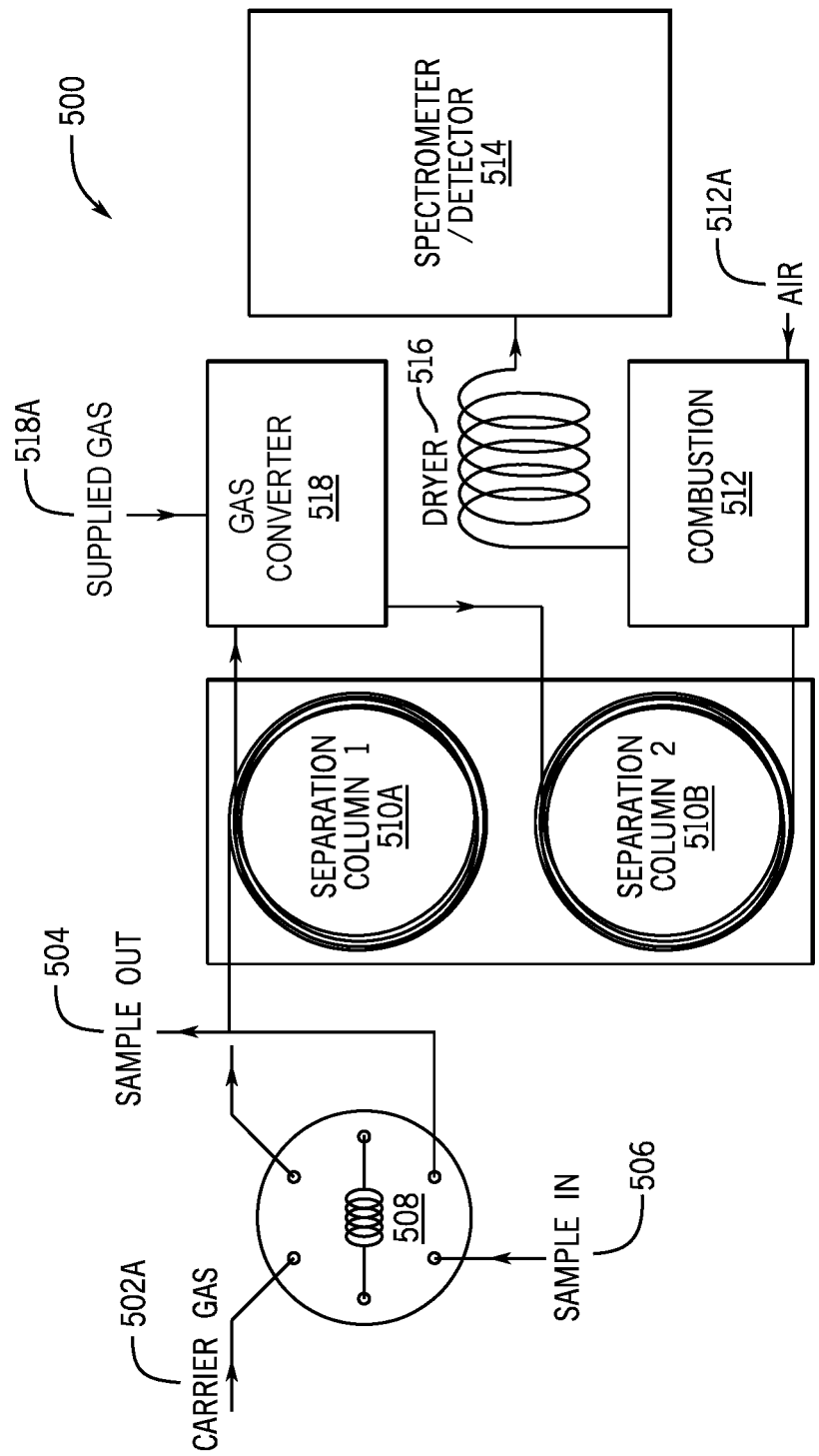
FIG. 5A illustrates a system for separation of components of a natural gas product according to at least one embodiment herein.

In at least one embodiment, FIG. 5A illustrates a system 500 for separation of components of a natural gas product that is an improvement over systems 200, 300, 400 previously discussed. In at least one embodiment, such a system may be referred to as a gas chromatography system with intermediate reaction (GC-IntR). In at least one embodiment, although parallel and series gas chromatography systems and methods may reduce separation time of components and may result in some reduction of a system cycle time, such a system cycle time remains long (such as, about 3-10 minutes in average). In at least one embodiment, characterization of reservoir layers may be based on carbon isotope ratios during drilling making such a system 500 a fast in-field chromatography system. In at least one embodiment, such a system may be dependent on a time resolution of isotope ratios in mud logs.

In at least one embodiment, an ultrafast gas chromatography system 500 enables improvement to time and chemical resolution from natural gas product samples. In at least one embodiment, such improvement leads to a better assessment of information that comes to a surface (such as surface or platform 108 in FIG. 1) during a drilling operation. In at least one embodiment, faster gas chromatography for spectrometers or other detectors 514 in a gas chromatography system 500 may be enabled by at least an intermediate reaction step provided by one or more gas converters 518. In at least one embodiment, such a gas converter 518 may be placed between one or more separation columns 510A; 510B.

In at least one embodiment, a gas converter may be a device adapted to exchange out (or convert) $CO_2$ to methane. In at least one embodiment, a gas converter may be a device adapted to exchange out (or convert) hydrogen sulfide ($H_2S$) to Sulphur dioxide ($SO_2$). In at least one embodiment, such exchanging out or converting features may be so that only isotopes of methane or $SO_2$ need to be detected in a spectrometer/detector to determine that a natural gas product has $CO_2$ or $H_2S$ components. In at least one embodiment, each of such converted component gas (methane or $SO_2$) may be of a different isotope than naturally available methane or $SO_2$ within a natural gas product. In at least one embodiment, a gas converter is a device adapted to reduce measurement time of components of a natural gas product from several minutes to below 1 minute by, for example, conversion of $CO_2$ to methane during a process for detecting C1-C5 and CO2 in a natural gas product; or conversion of $H_2S$ to $SO_2$ during a process for detecting C1-C5 and $H_2S$. In at least one embodiment, such a feature leads to better vertical resolution (during spectrometric analysis) in a drilling process and leads to better chemical resolution in mud gas analysis. Such improvements lead to faster decisions in near-real-time (NRT).

In at least one embodiment, a silica-fused column may be capable of separation of C1 to C5 within less than one (1) minute. In at least one embodiment, separation of $CO_2$ and ethane may not be possible due to overlapping of spectral peaks associated with these natural gas components. In at least one embodiment, $SO_2$ (converted from $H_2S$) may be readily measured in a detector for concentrations and/or for sulfur (S)-isotopes. $H_2S$ is a high Health, Safety, and Environment (HSE) risk and can make metals brittle. $H_2S$ may not be measured directly (differently than $CO_2$ and $CH_4$).

Further devices may be provided between separation columns to exchange or convert gasses to oxidized versions. In at least one embodiment, such oxidized versions may be measured for concentrations and/or for isotopes in a spectrometer. As such, it is possible to detect and measure various components of a natural gas product within a determined time period using gas converters between separation columns. For example, ammonium ($NH_4$), methane ($CH_4$), $H_2S$, and water vapor ($H_2O$) may be separated and measured in a similar manner using intervening gas converters. In an example, $H_2O$ may need separation of its elemental forms (such as, H and O) before measurements.

In one example, ammonium may become ammonia under a determined pH, in a solution. Ammonia may be oxidized in the presence of air (such as, in an oxygen rich environment) and in the presence of a catalyst to form nitrogen oxides. Furthermore, oxidizing continued in a gas converter for nitrogen oxides converts nitrogen oxides to nitrogen dioxide ($NO_2$). As such, a gas converter may be to oxidize a pH-changed ammonium (in ammonia form) to provide $NO_2$. In the manner of $CH_4$ and $SO_2$, detecting and measuring for concentrations and/or for nitrogen (N)-isotopes can provide information pertaining to ammonium in a natural gas product, and which may be detected by a system having separation columns and one or more gas converters for each of these components that are detected and measured faster by conversion than by separation.

In at least one embodiment, a gas converter 518 may be used to readily convert $CO_2$ to methane (or $H_2S$ to $S_2O$), which enables separation of spectral peaks of ethane (from a first separation column 510A) and $CO_2$-converted-methane (from a gas converter 518). In at least one embodiment, a preliminary separation therefore happens in a few meter of a silica-fused column of a first separation column 510A, which gives identical separated spectral peaks for each neighbor of a co-eluting $CO_2$-ethane spectral peak. In at least one embodiment, other than reaction in a gas converter 518, a final separation step occurs via a second separation column 510B using a few meters of silica-fused column to separate ethane and $CO_2$-converted-methane spectral peaks.

In at least one embodiment, a system 500 for separation of components of a natural gas product includes a first separation column 510A to receive a natural gas product (such as a natural gas product sample 506) and to provide first stage components. In at least one embodiment, a first separation column 510A receives its natural gas product from a combination chamber 508. In at least one embodiment, a carrier gas 502A may be provided to a combination chamber 508, along with a natural gas product sample 506, which is let out as a natural gas product sample 504, via a sample outlet. In at least one embodiment, a carrier gas may be hydrogen or helium.

In at least one embodiment, a first separation column 510A is adapted to receive a natural gas product and to provide first stage components that include at least a first methane and carbon dioxide (CO2). In at least one embodiment, ethane may share a similar spectral peak as such first methane from a first separation column 510A as illustrated in example peaks in FIG. 5B. In at least one embodiment, similarly, other hydrocarbons or byproducts may share a spectral peak with $H_2S$ and so fast in-field chromatography may be delayed but for a gas converter provided in a similar manner for $H_2S$ instead of $CO_2$.

As such, any hydrocarbons separated in a first separation column 510A remain unchanged as it passes through a gas converter 518 and the second separation column 510B (as well as in the combustion chamber 512 and the dryer 516. In at least one embodiment, only $CO_2$ or $H_2S$ are exchanged or converted as a stage of components pass out of a separation column (such as a first separation column 510A) over a multiple stage separation columns architecture. As such, a preliminary separation step (or one stage separation in a fast in-field chromatography system and method) results in C1-C5 components and $CO_2$. In such multiple stage separation columns architecture, two component gasses may overlap (such as $CO_2$ and Ethane).

A gas converter may be an intermediate separation step is able to convert or exchange out $CO_2$ to C1. Thereafter, one or more further separation steps can separation remaining stage components, while passing through previously separated component gasses (such as, C1, C1 from $CO_2$, $C_2$, and other hydrocarbons). In at least one embodiment, C1 from $CO_2$ comes after C1 (such as, detected after C1) in a spectrometer or detector output as a first separation column causes a delay by its separation process. Further from such separation steps, combustion is performed for all component gases using catalysts that are copper oxide (CuO)-based nickel oxide (NiO)-based, so that non-hydrocarbon component gases, such as CO2 is converted. Still further, drying of component gases with tube dryer, such as Nafion® may be performed. Finally, a measurement of $CO_2$, such as from a ratio of C12/C13 isotopes may be taken from spectrometer or detector. A measurement of $H_2S$ is similarly made from $SO_2$ isotope(s) determined from a spectrometer or detector.

In at least one embodiment, a gas converter 518 may receive such first stage components from a first separation column 510A and may be adapted to provide second stage components that include second methane. In at least one embodiment, previously provided first component gas (such as a first methane) may be passed-through such a gas converter 518. In at least one embodiment, such receiving and providing of natural gas components for each of system components 508-516 occurs at different periods of time or at different time points within a period of time.

In at least one embodiment, separations columns are provided to separate components (or component gasses) without converting them. As $CO_2$ and ethane have similar natural retention times, separation of these component gasses needs time. As such, different separation columns used for $CO_2$ and for ethane would add more time to a detection system and method. In at least one embodiment, separation is first performed to result in a combination of ethane and $CO_2$, from which $CO_2$ may be converted to CH4 so that a retention time for CH4 may be used instead without additional time.

Separated component gas from a first separation column may be directly passed to a combustion chamber followed by measurements of C1-C5 isotope ratios; and immediately thereafter $CO_2$-to-C1 converted component gas, delayed by the gas converted may be provided for the combustion chamber followed by associated measurements. There may be a further separation column to separate an original C1 from a $CO_2$-to-C1 converted component gas before other component gasses are received in a spectrometer/detector.

In at least one embodiment, second component gas (such as $CO_2$) from provided first stage components may be converted or provided as part of a second stage component in a form of a $CO_2$-converted-methane, referred to as a third component gas (or second methane). In at least one embodiment, $H_2S$ may be a second component gas and its conversion causes a third component gas that is $S_2O$. In at least one embodiment, such a third component gas (such as second methane) has spectral peaks that is distinct from ethane, but that was previously sharing a spectral peak with an unconverted form of such second component gas (such as $CO_2$). In at least one embodiment, such $CO_2$-converted-methane (or any third component gas) may be passed-through a second separation column 510B without further reaction, in a similar manner as a first component gas (such as methane) that may be passed through both a gas converter 518 and a second separation column 510B without further reaction.

In at least one embodiment, a second separation column 510B may be adapted to receive second stage components from a gas converter 518 and may be adapted to provide third stage components. In at least one embodiment, such third stage components include a first component gas (such as first methane) from a first separation column 510A, a third component gas (such as second methane) from a gas converter 518, and one or more additional carbon-based components from a first separation column 510A of from a second separation column 510B. In at least one embodiment, individual second stage components and individual third stage components may be provided at or over a period of time that is associated with such separation of such components of a natural gas product 506. In at least one embodiment, multiple gas converters may be used in series so that each of $CO_2$ and $H_2S$ may be converted by such a system.

In at least one embodiment, a hydrogen or oxygen source may be provided in a fast in-field chromatography system 500. In at least one embodiment, a hydrogen source may be for providing hydrogen gas as the supplied gas 518A to a gas converter 518 to support conversion of carbon dioxide ($CO2$) of first stage components to a second methane, where such first stage components already include a first methane. In at least one embodiment, an oxygen source may be for providing hydrogen gas as the supplied gas 518A to support conversion of $H_2S$ of first stage components to $S_2O$.

In at least one embodiment, such first stage components are provided on or at different time points in a period of time or on or at different time periods. In at least one embodiment, reference to providing first, second, and third stage components, from a first separation column, a gas converter, and a second separation column, may be to components passed-through or formed within one or more of such first separation column, gas converter, or second separation column. In at least one embodiment, first methane separated in a first separation column is passed through a gas converter and a second separation column, without further changes or reaction performed thereon.

In a combustion chamber, all hydrocarbon component gasses may be transformed to $CO_2$, which may be then measured in a spectrometer for isotope ratios, such as for C12/C13. Further, hydrocarbon component gasses do not react, convert, or exchange out within a gas converter. As such, only $CO_2$ (or $H_2S$, where appropriate) is exchanged out or converted in the gas converter. Still further, a first component gas (C1) and a third component gas (such as a CO2-converted-C1) may be separated in a second column before a combustion chamber.

In at least one embodiment, a fast in-field chromatography system 500 includes a gas converter 518 that provides one or more additional carbon-based components than a first methane, and may be adapted to provide such one or more additional carbon-based components as pass-through components, which are as provided to it from a first separation column 510A. In at least one embodiment, such a gas converter may be separately provided to output one or more sulfur-base components along with carbon-based components as pass-through components of a prior separation column.

In at least one embodiment, a fast in-field chromatography system 500 includes a combustion chamber 512 and a dryer 516 to condition third stage components (from a second separation column 510B) for a spectrometer or detector 514. In at least one embodiment, a spectrometer or detector 514 may be adapted to provide results associated with peaks of individual isotopes of individual third stage components versus time of detection or measurement of such individual third stage components. In at least one embodiment, such individual third stage components include at least some of individual first stage components (from a first separation column 510A) and at least some of such individual second stage components (from a gas converter 518)

In at least one embodiment, a fast in-field chromatography system 500 includes a spectrometer or a detector 514 to register a first methane as a different isotope than a second methane or to register different spectral peaks at different times for a first methane and a second methane, where such second methane is a $CO_2$-converted-methane from a gas converter.

In at least one embodiment, a fast in-field chromatography system 500 includes a gas converter 518 to enable separation of ethane and CO2 from a first separation column 510A. In at least one embodiment, such conversion may be enabled, in part, by a conversion of such $CO_2$ to second methane in presence of a catalyst and supplied hydrogen gas. In at least one embodiment, such second methane is distinct from first methane separation in a first separation column 510A from a natural gas product provided to it.

Figure 8:
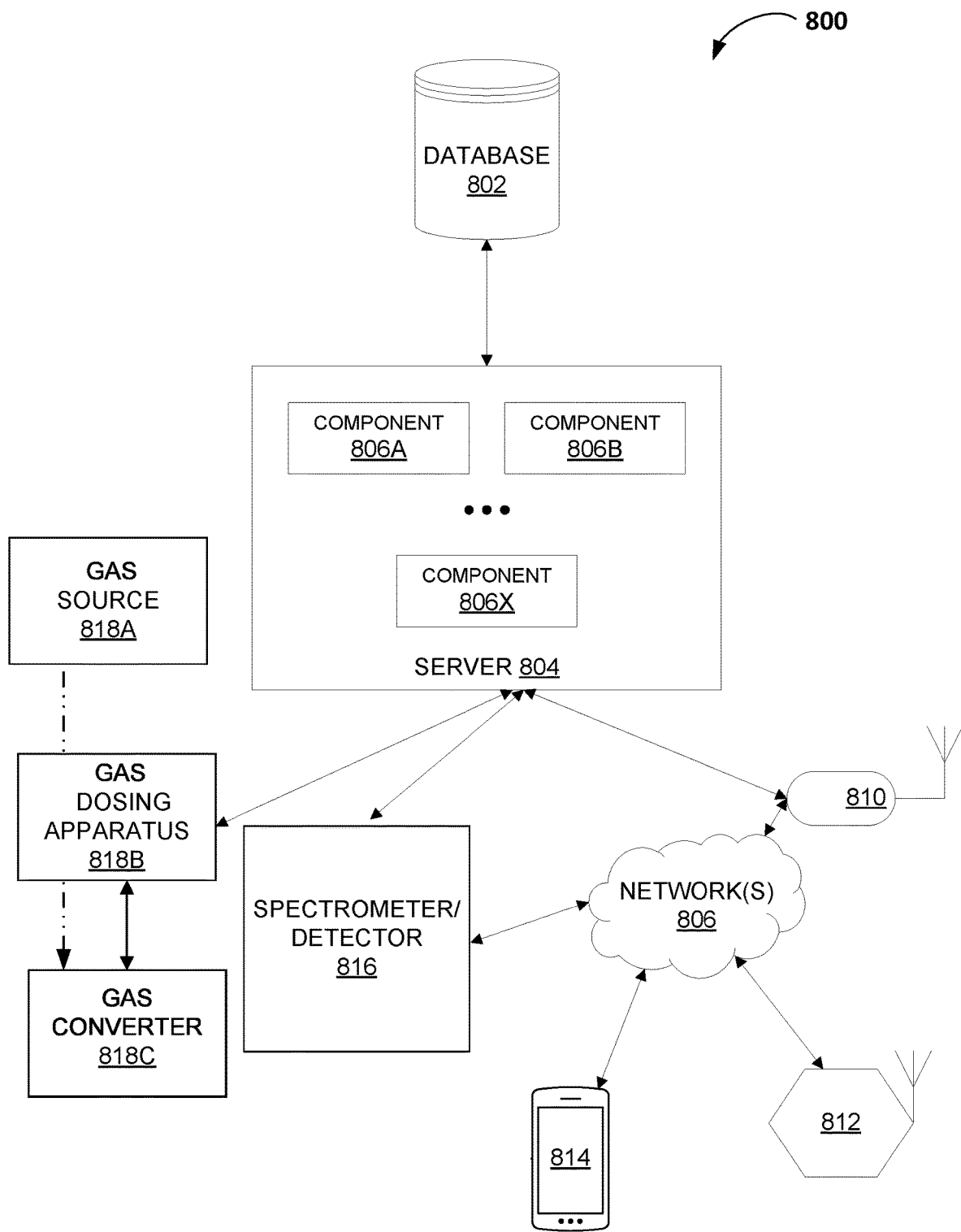
FIG. 8 illustrates computer and network aspects for a fast in-field chromatography system, according to at least one embodiment.

In at least one embodiment, a fast in-field chromatography system 500 includes a hydrogen, oxygen, or other gas dosing apparatus to be associated with at least one processor and memory comprising instructions that when executed by at least one processor enables a hydrogen or oxygen dosing apparatus to control delivery of hydrogen, oxygen, or other gas to a gas converter (such as illustrated in FIG. 8). In at least one embodiment, a fast in-field chromatography system 500 includes a combustion chamber 512 to chemically reduce, by reaction in presence of at least a copper oxide (CuO)-based catalyst, natural gas of third stage components. In at least one embodiment, such a CuO-based catalyst may be regenerated periodically.

In at least one embodiment, a gas converter 518 is able to provide second stage components by conversion of at least $CO_2$ in first stage components of a first separation column 510A by using hydrogen supplied gas 518A provided to it. In at least one embodiment, a reaction (equation 1) may occur within a gas converter 518.

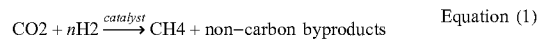

$$CO2 + nH2 \xrightarrow{catalyst} CH4 + \text{non-carbon byproducts} \quad \text{Equation (1)}$$

In at least one embodiment, hydrogen supplied gas 518A is a reactant in this reaction. In at least one embodiment, injection of hydrogen supplied gas 518A occurs in a programmed, well-dosed approach, so that excess hydrogen cannot reach a combustion chamber 512 after a separation step occurs subsequent to a second separation column 510B. In at least one embodiment, catalytic combustion in a combustion chamber 512 occurs in presence of a copper oxide (CuO) or Nickel oxide (NiO) catalyst. In at least one embodiment, such a catalyst may be produced from copper or nickel foam oxidization. In at least one embodiment, an operation as such enables CuO or NiO to be converted to Cu or Ni in a reduction reaction with natural gas of second stage components and with hydrogen possibly entering to a combustion module 512. While limited, such entry of hydrogen may occur. Alternatively, helium may be used a carrier gas, but a separation process may be slower as helium may flow slower than hydrogen.

In at least one embodiment, a gas converter 518 is able to provide second stage components by conversion of at least $H_2S$ in first stage components of a first separation column 510A by using oxygen supplied gas 518A provided to it. In at least one embodiment, a reaction (equation 2) may occur within a gas converter 518

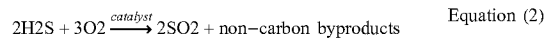

$$2H2S + 3O2 \xrightarrow{catalyst} 2SO2 + \text{non-carbon byproducts} \quad \text{Equation (2)}$$

In at least one embodiment, oxygen supplied gas 518A is a reactant in this reaction. In at least one embodiment, injection of oxygen supplied gas 518A occurs in a programmed, well-dosed approach, so that excess oxygen cannot reach a combustion chamber 512 after a separation step occurs subsequent to a second separation column 510B. In at least one embodiment, catalytic combustion in a combustion chamber 512 occurs in presence of a CuO or NiO catalyst.

In at least one embodiment, such a catalyst may be produced from copper or nickel foam oxidization. In at least one embodiment, an operation as such enables CuO or NiO to be converted to Cu or Ni in a reduction reaction with natural gas of second stage components and with oxygen possibly entering to a combustion module 512. While limited, such entry of oxygen may occur.

In at least one embodiment, a non-carbon byproduct from a gas converter 518 is water. In at least one embodiment, such water may be removed in a dryer 516, which may be a catalytic tube dryer. In at least one embodiment, for improved lifetime of a combustion module 512, a catalyst applied therein may be regenerated with blown air to cause thermal oxidation of copper in 2 hours at 500° C. In at least one embodiment, two combustion chambers 512 may be provided as two catalytic combustion modules, so that one module may be in service and another module may be in regeneration mode at any point in time. In at least one embodiment, for improving stability, linearity, and reproducibility of such a system 500, a calibration point may be suggested after switching of a combustion chamber 512.

In at least one embodiment, a fast in-field chromatography system 500 includes a spectrometer or detector 514 (also as illustrated and described with respect to FIG. 8) to include a determined calibration point to enable repeatable detection of components of a natural gas product. In at least one embodiment, a fast in-field chromatography system 500 includes a spectrometer or detector 514 that may be associated with a combustion chamber 512 that receives air 512A to assist the combustion. In at least one embodiment, a spectrometer or detector 514 is adapted to include a determined calibration point to enable repeatable detection of components of a natural gas product after individual regeneration of a catalyst of a combustion chamber 512.

Figure 5B:
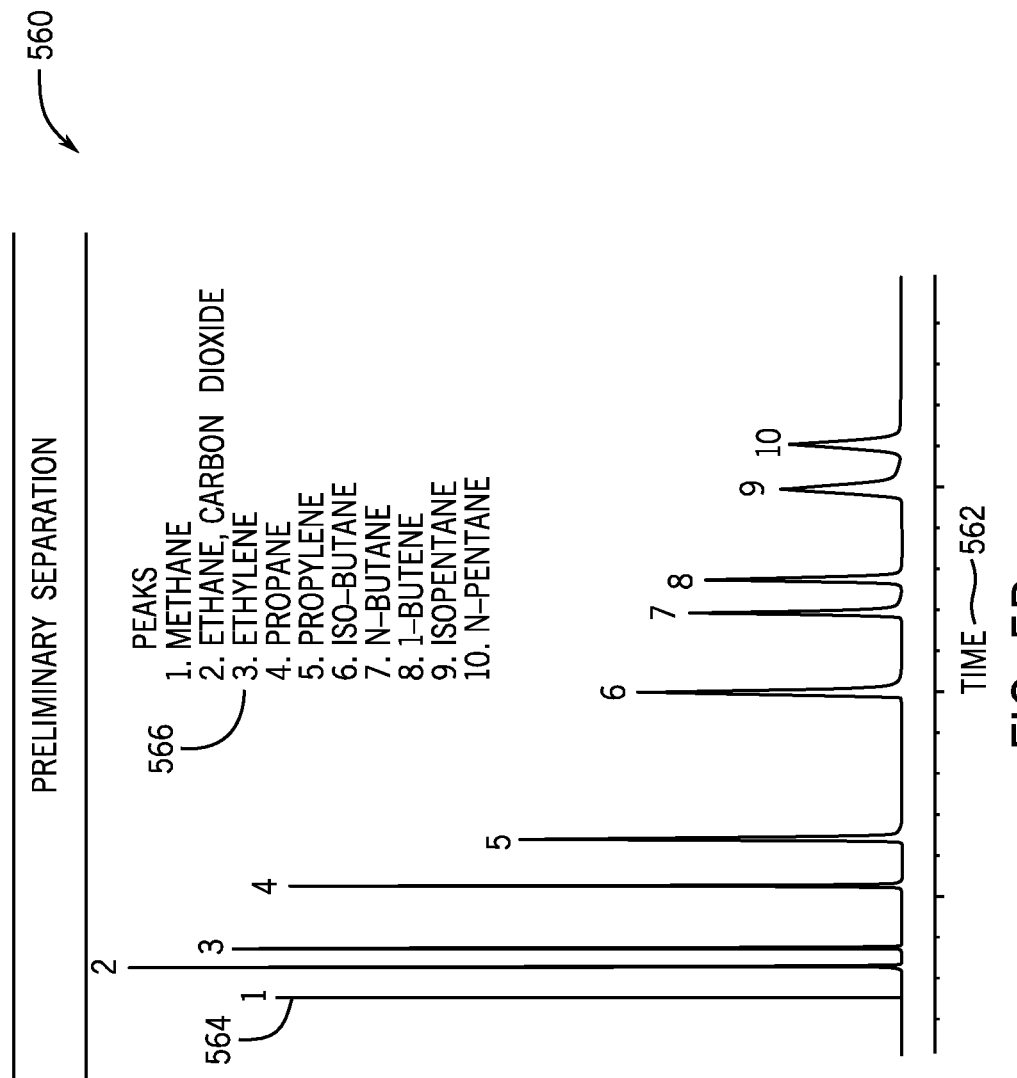
Figure 5C:
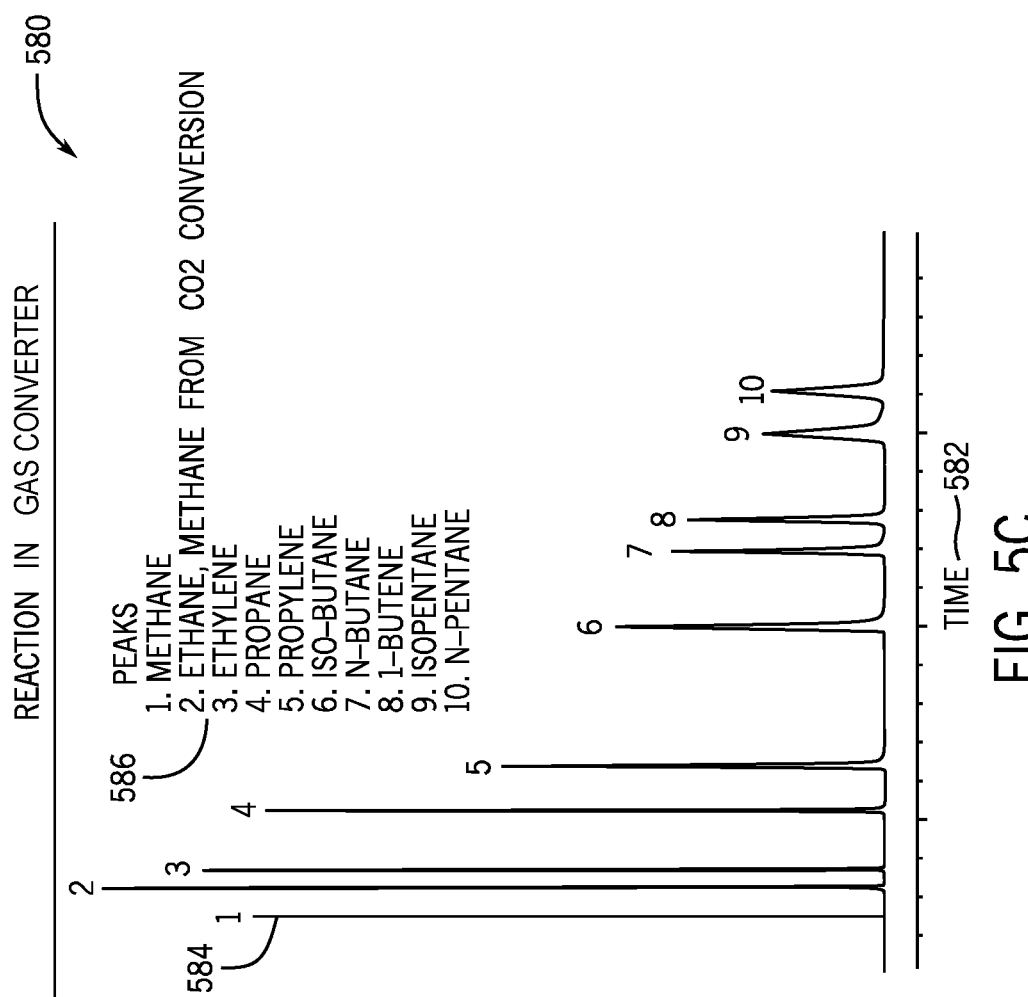

FIGS. 5B-D illustrate results 560, 580, 590 from a system 500 for separation of components of a natural gas product, such as described in FIG. 5A, of at least one embodiment herein. In at least one embodiment, such figures are of different stage results of a system 500 in FIG. 5A for isotope ratio measurement of C1 to C5 plus $CO_2$. In at least one embodiment, an overall cycle time of separation and detection of C1 to C5 components of a natural gas product, plus $CO_2$, is within 1 minute.

In FIG. 5B, first stage components' spectral peaks 564 are illustrated with a label 566, for each spectral peak, as measured from output of a first separation column, in a system 500 in FIG. 5A. In at least one embodiment, detection of first stage components, including a first methane (label 1), a final first stage component, n-pentane (label 10), along with mixed peaks for ethane and $CO_2$ (labeled 2), are illustrated. In at least one embodiment, a timeline 562 of plot 560 illustrates such a mixed peak. In FIG. 5C, second stage components' spectral peaks 584 are illustrated with a label 586, for each spectral peak, for a system 500 in FIG. 5A. As illustrated, in at least one embodiment, detection of second stage components, including of a first methane ethane (label 1, which may be a pass-through from first stage components), along with a mixed peak of ethane and second methane (label 2, $CO_2$-converted-methane) are illustrated on a timescale 582 of plot 580.

In FIG. 5D, according to at least one embodiment, third stage components' spectral peaks 594 are illustrated with a label 596, for each spectral peak, for a system 500 in FIG. 5A. In FIG. 5C, first methane (label 1), second methane (label 2), and ethane (label 3) are all illustrated as separate spectral peaks (after a second separation column) as detected by a spectrometer or detector following combustion and drying. Also as illustrated, detection of a final natural gas component, n-pentane (label 11), occurs under a one (1) minute mark per a minute scale 592 of plot 590. In at least one embodiment, a system and method herein can cause a third component gas (such as the $CO_2$-converted-C1) in roughly 10 seconds, and then flow through a combustion chamber, along with a measurement on a spectrometer or detector, could be completed in few more seconds. This results in a sub-1 minute or 1 minute separation and detection of all component gasses in a natural gas product as indicated in the x-axis scale in FIG. 5D.

Figure 6:
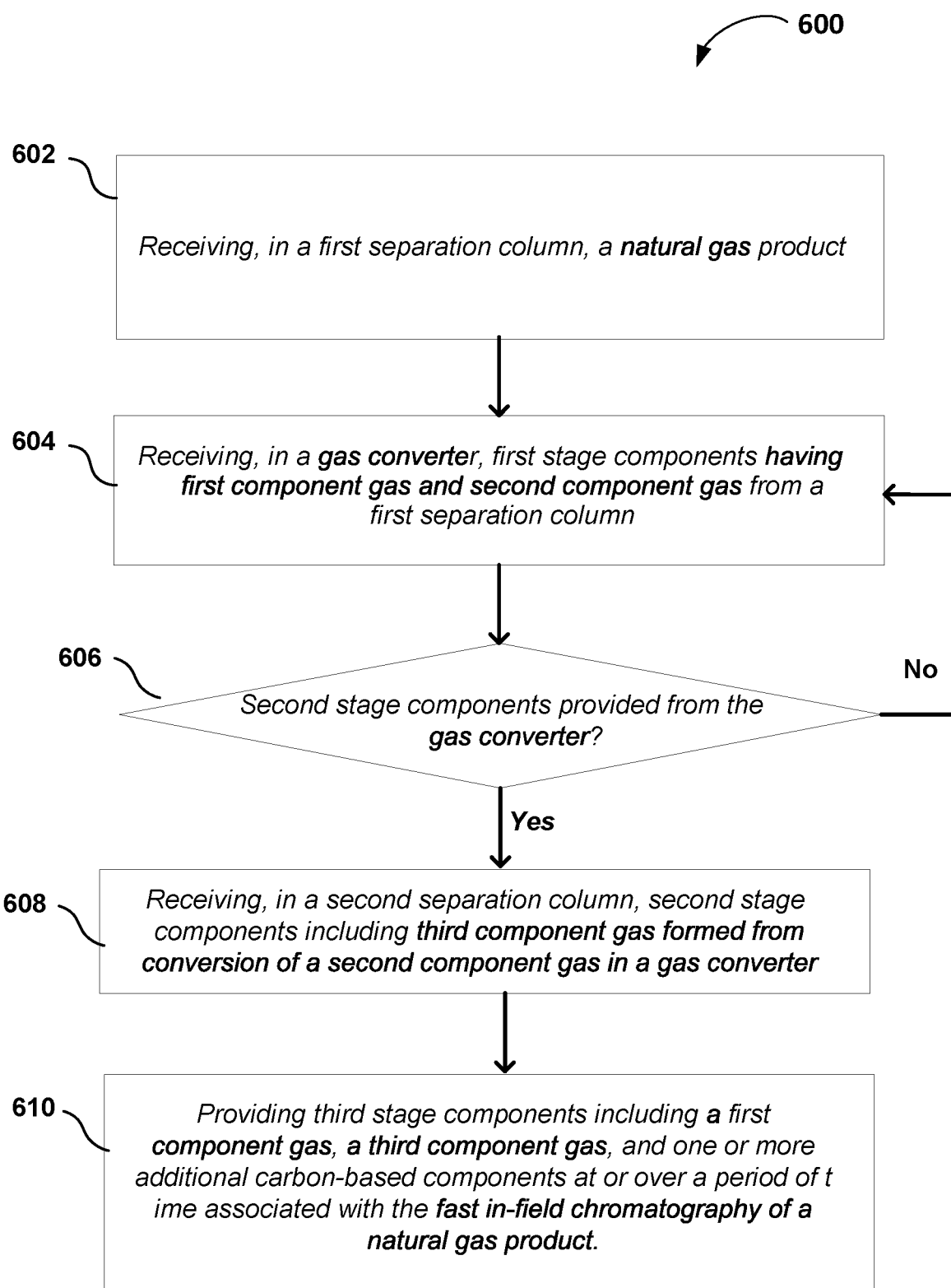
FIG. 6 illustrates a process flow of a method for separation of components of a natural gas product according to at least one embodiment herein.

FIG. 6 illustrates a process flow of a method 600 for separation of components of a natural gas product according to at least one embodiment herein. In at least one embodiment, step 602 is for receiving a natural gas product in a first separation column. In at least one embodiment, step 604 is for receiving first stage components from a first separation column to a or in a gas converter. In at least one embodiment, such first stage components include at least a first component gas (such as first methane) and a second component gas (such as carbon dioxide ($CO_2$)). In at least one embodiment, $H_2S$ is a second component gas received in a gas converter via step 604 and in which it is converted to a third component gas ($S_2O$) in a gas converter In at least one embodiment, step 606 is a determination step to verify that second stage components are provided from a gas converter. In at least one embodiment, if step 606 is verified, step 608 is performed for receiving, in a second separation column, second stage components that includes first component gas (such as first methane) and a third component gas (such as second methane). In at least one embodiment, such second methane may be formed from $CO_2$ received to a gas converter in step 604. In at least one embodiment, step 604 may be repeated if a verification in step 606 fails.

In at least one embodiment, step 610 is for providing, from a second separation column, third stage components that includes first component gas (such as first methane), third component gas (such as second methane), and one or more additional carbon-based components. In at least one embodiment, such individual second stage components and such individual third stage components are provided at or over a period of time associated with a separation of components of a natural gas product.

Figure 7:
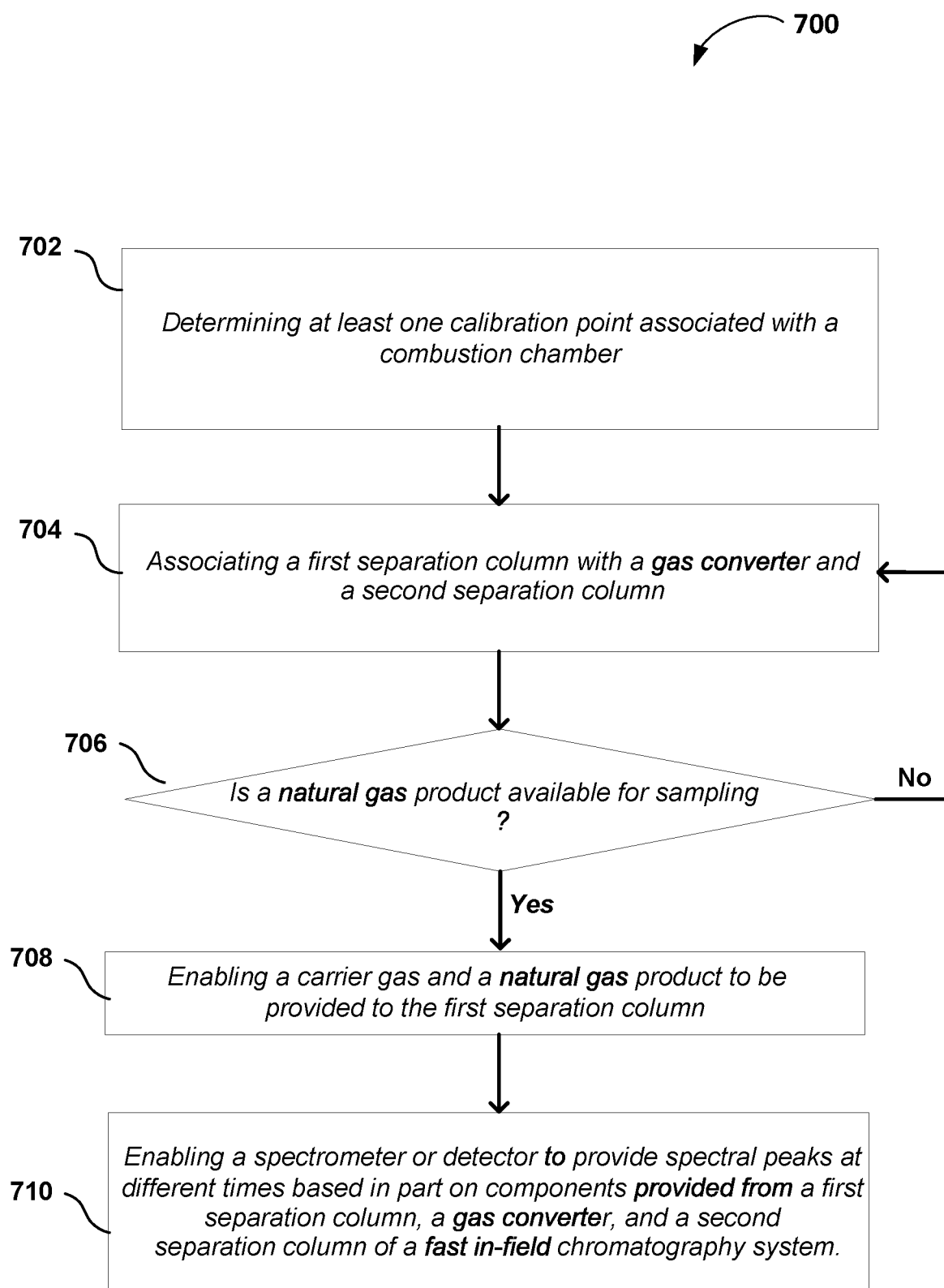
FIG. 7 illustrates another process flow of a method for separation of components of a natural gas product according to at least one embodiment herein.

FIG. 7 illustrates another process flow of a method 700 for separation of components of a natural gas product according to at least one embodiment herein. In at least one embodiment, method 700 includes step 702 for determining at least one calibration point associated with a combustion chamber and may be done with respect to a spectrometer or a detector. In at least one embodiment, step 702 may include enabling a spectrometer or detector to include a determined calibration point that is then associated with a combustion chamber. In at least one embodiment, such a determination supports enabling repeatable detection of components of a natural gas product based in part on such a determined calibration point.

In at least one embodiment, method 700 includes a step 704 for associating a first separation column with a gas converter and a second separation column. In at least one embodiment, a sub-step of step 704 includes associating a spectrometer or detector with a combustion chamber so that such a spectrometer or detector is able to include a determined calibration point. In at least one embodiment, such a feature includes enabling repeatable detection of components (or component gasses) of a natural gas product after individual regeneration of a catalyst of a combustion chamber, where a fast in-filed chromatography system has to be restarted after a combustion chamber is replaced or its catalyst is replaced (or regenerated).

In at least one embodiment, step 706 may be a verification step for determining that natural gas product is available sampling, such as following startup of a fast in-filed chromatography system. In at least one embodiment, an association step 704 may be otherwise repeated. In at least one embodiment, step 708 may be enabled for carrier gas and natural gas product to be provided to a first separation chamber. In at least one embodiment, step 710 may be provided for enabling a spectrometer or detector to provide different spectral peaks at different types based in part on components (or component gasses) provided from a first separation column, a gas converter, and a second separation column. In at least one embodiment, conversion of $CO_2$ to a second methane may be referred to as a separation of second methane from ethane that would have otherwise offered overlapping peaks between ethane and $CO_2$ of a natural gas product.

In at least one embodiment, computer and network aspects 800 for a fast in-field chromatography system as illustrated in FIG. 8, may be used as described herein. In at least one embodiment, these computer and network aspects 800 may include a distributed system. In at least one embodiment, a distributed system 800 may include one or more computing devices 812-816. In at least one embodiment, one or more computing devices 812-816 may be adapted to execute and function with a client application, such as with browsers or a stand-alone application, and are adapted to execute and function over one or more network(s) 806.

In at least one embodiment, a server 804, having components 806A-X may be communicatively coupled with computing devices 812-816 via network 806 and via a receiver device 810, if provided. In at least one embodiment, components 806A-X include processors, memory and random access memory (RAM). In at least one embodiment, server 804 may be adapted to operate services or applications to manage functions and sessions associated with database access 802 and associated with computing devices 812-816. In at least one embodiment, server 804 may be associated with a receiver device and a monitor device. In at least one embodiment, server 804 may be at a wellsite location, but may also be at a distinct location from a wellsite location. In at least one embodiment, such a server 804 may support a spectrometer or detector 816 and/or a gas (such as hydrogen or oxygen) dosing apparatus 818B that may be adapted to deliver doses of hydrogen, oxygen, or other gas, from a gas source 818A to a gas converter 818C. In at least one embodiment, a sensor may be associated with a gas converter 818C to communicate back to a gas dosing apparatus 818B and to a server 804 regarding dosage applied or to be applied.

In at least one embodiment, a monitor device and/or a receiver device is adapted to transmit, either through wires or wireless, information received therein, including dosage information and results from a spectrometer or detector. In at least one embodiment, such information may be received in a receiver device and transmitted to a monitor device that infers from changes in electrical properties based in part on instructions stored therein. In at least one embodiment, a server 804 may function as a monitor device but may also perform other functions. In at least one embodiment, one or more component 806A-X may be adapted to function as a monitor device within a server 804. In at least one embodiment, one or more components 806A-X and 818B may include one or more processors and one or more memory devices adapted to function as a monitor device, while other processors and memory devices in server 804 may perform other functions.

In at least one embodiment, server 804 may also provide services or applications that are software-based in a virtual or a physical environment. In at least one embodiment, when server 804 is a virtual environment, then components 806A-X are software components that may be implemented on a cloud. In at least one embodiment, this feature allows remote operation of receiver devices, spectrometers or detectors, and of a hydrogen dosing apparatus, as discussed at least in reference to FIGS. 5A-D. In at least one embodiment, this feature also allows for remote access to information received and communicated between any of aforementioned devices. In at least one embodiment, one or more components 806A-X of a server 804 may be implemented in hardware or firmware, other than a software implementation described throughout herein. In at least one embodiment, combinations thereof may also be used.

In at least one embodiment, one computing device 816 may be a smart monitor or a display having at least a microcontroller and memory having instructions to enable display of information monitored by a monitor device and received by a receiver device. In at least one embodiment, one computing device 812 may be a transmitter device to transmit directly to a receiver device 810 or to transmit via a network 806 to a receiver device 810 and to a server 804, as well as to other computing devices 814. In at least one embodiment, other computing devices 814 may include portable handheld devices that are not limited to smartphones, cellular telephones, tablet computers, personal digital assistants (PDAs), and wearable devices (head mounted displays, watches, etc.). In at least one embodiment, other computing devices 814 may operate one or more operating systems including Microsoft Windows Mobile®, Windows® (of any generation), and/or a variety of mobile operating systems such as iOS®, Windows Phone®, Android®, BlackBerry®, Palm OS®, and/or variations thereof.

In at least one embodiment, other computing devices 814 may support applications designed as internet-related applications, electronic mail (email), short or multimedia message service (SMS or MMS) applications, and may use other communication protocols. In at least one embodiment, other computing devices 814 may also include general purpose personal computers and/or laptop computers running such operating systems as Microsoft Windows®, Apple Macintosh®, and/or Linux®. In at least one embodiment, other computing devices 814 may be workstations running UNIX® or UNIX-like operating systems or other GNU/Linux operating systems, such as Google Chrome OS®. In at least one embodiment, thin-client devices, including gaming systems (Microsoft Xbox®) may be used as other computing device 814.

In at least one embodiment, network(s) 806 may be any type of network that can support data communications using various protocols, including TCP/IP (transmission control protocol/Internet protocol), SNA (systems network architecture), IPX (Internet packet exchange), AppleTalk®, and/or variations thereof. In at least one embodiment, network(s) 806 may be a networks that is based on Ethernet, Token-Ring, a wide-area network, Internet, a virtual network, a virtual private network (VPN), a local area network (LAN), an intranet, an extranet, a public switched telephone network (PSTN), an infra-red network, a wireless network (such as that operating with guidelines from an institution like the Institute of Electrical and Electronics (IEEE) 802.11 suite of protocols, Bluetooth®, and/or any other wireless protocol), and/or any combination of these and/or other networks.

In at least one embodiment, a server 804 runs a suitable operating system, including any of operating systems described throughout herein. In at least one embodiment, server 804 may also run some server applications, including HTTP (hypertext transport protocol) servers, FTP (file transfer protocol) servers, CGI (common gateway interface) servers, JAVA® servers, database servers, and/or variations thereof. In at least one embodiment, a database 802 is supported by database server feature of a server 804 provided with front-end capabilities. In at least one embodiment, such database server features include those available from Oracle®, Microsoft®, Sybase®, IBM® (International Business Machines), and/or variations thereof.

In at least one embodiment, a server 804 is able to provide feeds and/or real-time updates for media feeds. In at least one embodiment, a server 804 is part of multiple server boxes spread over an area, but functioning for a presently described process for fast in-field chromatography. In at least one embodiment, server 804 includes applications to measure network performance by network monitoring and traffic management. In at least one embodiment, a provided database 802 enables information storage from a wellsite, including user interactions, usage patterns information, adaptation rules information, and other information.

While techniques herein may be subject to modifications and alternative constructions, these variations are within spirit of present disclosure. As such, certain illustrated embodiments are shown in drawings and have been described above in detail, but these are not limiting disclosure to specific form or forms disclosed; and instead, cover all modifications, alternative constructions, and equivalents falling within spirit and scope of disclosure, as defined in appended claims.

Terms such as a, an, the, and similar referents, in context of describing disclosed embodiments (especially in context of following claims), are understood to cover both singular and plural, unless otherwise indicated herein or clearly contradicted by context, and not as a definition of a term. Including, having, including, and containing are understood to be open-ended terms (meaning a phrase such as, including, but not limited to) unless otherwise noted. Connected, when unmodified and referring to physical connections, may be understood as partly or wholly contained within, attached to, or joined together, even if there is something intervening.

Recitation of ranges of values herein are merely intended to serve as a shorthand method of referring individually to each separate value falling within range, unless otherwise indicated herein and each separate value is incorporated into specification as if it were individually recited herein. In at least one embodiment, use of a term, such as a set (for a set of items) or subset unless otherwise noted or contradicted by context, is understood to be nonempty collection including one or more members. Further, unless otherwise noted or contradicted by context, term subset of a corresponding set does not necessarily denote a proper subset of corresponding set, but subset and corresponding set may be equal.

Conjunctive language, such as phrases of form, at least one of A, B, and C, or at least one of A, B and C, unless specifically stated otherwise or otherwise clearly contradicted by context, is otherwise understood with context as used in general to present that an item, term, etc., may be either A or B or C, or any nonempty subset of set of A and B and C. In at least one embodiment of a set having three members, conjunctive phrases, such as at least one of A, B, and C and at least one of A, B and C refer to any of following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present. In addition, unless otherwise noted or contradicted by context, terms such as plurality, indicates a state of being plural (such as, a plurality of items indicates multiple items). In at least one embodiment, a number of items in a plurality is at least two, but can be more when so indicated either explicitly or by context. Further, unless stated otherwise or otherwise clear from context, phrases such as based on means based at least in part on and not based solely on.

Operations of methods 600 and 700 or sub-steps described herein can be performed in any suitable order unless otherwise indicated herein or otherwise clearly contradicted by context. In at least one embodiment, a method includes processes such as those processes described herein (or variations and/or combinations thereof) that may be performed under control of one or more computer systems configured with executable instructions and that may be implemented as code (e.g., executable instructions, one or more computer programs or one or more applications) executing collectively or exclusively on one or more processors, by hardware or combinations thereof.

In at least one embodiment, such code may be stored on a computer-readable storage medium. In at least one embodiment, such code may be a computer program having instructions executable by one or more processors. In at least one embodiment, a computer-readable storage medium is a non-transitory computer-readable storage medium that excludes transitory signals (such as a propagating transient electric or electromagnetic transmission) but includes non-transitory data storage circuitry (such as buffers, cache, and queues) within transceivers of transitory signals. In at least one embodiment, code (such as executable code or source code) is stored on a set of one or more non-transitory computer-readable storage media having stored thereon executable instructions (or other memory to store executable instructions) that, when executed (such as a result of being executed) by one or more processors of a computer system, cause computer system to perform operations described herein.

In at least one embodiment, a set of non-transitory computer-readable storage media includes multiple non-transitory computer-readable storage media and one or more of individual non-transitory storage media of multiple non-transitory computer-readable storage media lack all of code while multiple non-transitory computer-readable storage media collectively store all of code. In at least one embodiment, executable instructions are executed such that different instructions are executed by different processors—in at least one embodiment, a non-transitory computer-readable storage medium store instructions and a main central processing unit (CPU) executes some of instructions while other processing units execute other instructions. In at least one embodiment, different components of a computer system have separate processors and different processors execute different subsets of instructions.

In at least one embodiment, computer systems are configured to implement one or more services that singly or collectively perform operations of processes described herein and such computer systems are configured with applicable hardware and/or software that enable performance of operations. In at least one embodiment, a computer system that implements at least one embodiment of present disclosure is a single device or is a distributed computer system having multiple devices that operate differently such that distributed computer system performs operations described herein and such that a single device does not perform all operations.

In at least one embodiment, even though the above discussion provides at least one embodiment having implementations of described techniques, other architectures may be used to implement described functionality, and are intended to be within scope of this disclosure. In addition, although specific responsibilities may be distributed to components and processes, they are defined above for purposes of discussion, and various functions and responsibilities might be distributed and divided in different ways, depending on circumstances.

In at least one embodiment, although subject matter has been described in language specific to structures and/or methods or processes, it is to be understood that subject matter claimed in appended claims is not limited to specific structures or methods described. Instead, specific structures or methods are disclosed as example forms of how a claim may be implemented.

From all the above, a person of ordinary skill would readily understand that the tool of the present disclosure provides numerous technical and commercial advantages, and can be used in a variety of applications. Various embodiments may be combined or modified based in part on the present disclosure, which is readily understood to support such combination and modifications to achieve the benefits described above.

What is claimed is:

1. A system for separation of components of a natural gas product, the system comprising:
    a gas converter to receive first stage components separated from the natural gas product and to provide second stage components that comprise a first component gas from the first stage components and a third component gas that is formed in the gas converter, the third component gas formed by conversion of a second component gas of the first stage components; and
    a separation column to receive the second stage components and to provide third stage components, the third stage components comprising the first component gas, the third component gas, and one or more additional carbon-based components, wherein individual second stage components and individual third stage components are provided in or over a period of time associated with the separation of the components of the natural gas product.

2. The system of claim 1, wherein the second component gas is carbon dioxide ($CO_2$), ammonium ($NH_4$), or hydrogen sulfide ($H_2S$).

3. The system of claim 1, further comprising one or more of:
    a hydrogen source to provide hydrogen gas to the gas converter; or
    an oxygen source to provide oxygen gas to the gas converter.

4. The system of claim 1, further comprising:
    a combustion chamber and a dryer to condition the third stage components for a spectrometer or detector, the spectrometer or detector to provide results associated with spectral peaks of individual isotopes of the individual third stage components versus time of detection or measurement of the individual third stage components.

5. The system of claim 1, further comprising:
    a spectrometer or detector to register the first component gas as a first methane and the third component gas as a second methane of a different isotope than the first methane; or
    the spectrometer or detector to register different spectral peaks at different times for the first component gas and the third component gas.

6. The system of claim 1, wherein the gas converter is further configured to:
    enable separation of spectral peaks associated with ethane and the second component gas, in part, by a conversion of the second component gas to the third component gas in presence of a catalyst and a supplied gas, the second component gas being $CO_2$ or $H_2S$, the third component gas being methane or $SO_2$, and the supplied gas being hydrogen gas or oxygen gas.

7. The system of claim 1, further comprising:
    a hydrogen or oxygen dosing apparatus to be associated with at least one processor and memory comprising instructions that when executed by the at least one processor enables the hydrogen or oxygen dosing apparatus to control delivery of hydrogen gas or oxygen gas to the gas converter.

8. The system of claim 1, further comprising:
    a combustion chamber to chemically reduce, by reaction in presence of at least a copper oxide (CuO)-based catalyst, natural gas of the third stage components, wherein the CuO-based catalyst is to be regenerated periodically.

9. The system of claim 1, further comprising:
    a spectrometer or detector to comprise a determined calibration point to enable repeatable detection of the components of the natural gas product.

10. The system of claim 1, further comprising:
    a spectrometer or detector associated with a combustion chamber, the spectrometer or detector to comprise a determined calibration point to enable repeatable detection of the components of the natural gas product after individual regeneration of a catalyst of the combustion chamber.

11. A method for separation of components of a natural gas product, the method comprising:
    receiving, in a gas converter, first stage components separated from the natural gas product;
    providing second stage components that comprise a first component gas from the first stage components and a third component gas that is formed in the gas converter, the third component gas formed by conversion of a second component gas of the first stage components; and
    receiving, in a separation column, the second stage components; and
    providing third stage components comprising the first component gas, the third component gas, and one or more additional carbon-based components, wherein individual second stage components and individual third stage components are provided in or over a period of time associated with the separation of the components of the natural gas product.

12. The method of claim 11, wherein the second component gas is carbon dioxide ($CO_2$), ammonium ($NH_4$), or hydrogen sulfide ($H_2S$).

13. The method of claim 11, further comprising:
    providing, using a hydrogen source, hydrogen gas to the gas converter; or
    providing, using an oxygen source, oxygen gas to the gas converter.

14. The method of claim 11, further comprising:
conditioning the third stage components using a combustion chamber and a dryer;
providing the third stage components, after conditioning, to a spectrometer or detector; and
providing results from the spectrometer or detector, the results associated with spectral peaks of individual isotopes of the individual third stage components versus time of detection or measurement of the individual third stage components.

15. The method of claim 11, further comprising:
registering, using a spectrometer or detector, the first component gas as a first methane and the third component gas as a second methane of a different isotope than the first methane; or
registering different spectral peaks at different times for the first component gas and the third component gas.

16. The method of claim 11, further comprising:
enabling separation of spectral peaks of ethane and the second component gas, in part, by a conversion of the second component gas to the third component gas, in the gas converter, in presence of a catalyst and supplied gas, the second component gas being $CO_2$ or $H_2S$, the third component gas being methane or $SO_2$, and the supplied gas being hydrogen gas or oxygen gas.

17. The method of claim 11, further comprising:
enabling a hydrogen or oxygen dosing apparatus to be associated with at least one processor and memory comprising instructions; and
enabling, by the hydrogen or oxygen dosing apparatus, when the instructions are executed by the at least one processor, controlled delivery of hydrogen gas or oxygen gas to the gas converter.

18. The method of claim 11, further comprising:
chemically reducing, in a combustion chamber and by reaction in presence of at least a copper oxide (CuO)-based catalyst, natural gas of the third stage components, the CuO-based catalyst to be regenerated periodically.

19. The method of claim 11, further comprising:
enabling a spectrometer or detector to comprise a determined calibration point; and
enabling repeatable detection of the components of the natural gas product based in part on the determined calibration point, based in part on the determined calibration point.

20. The method of claim 11, further comprising:
associating a spectrometer or detector with a combustion chamber, the spectrometer or detector to comprise a determined calibration point; and
enabling repeatable detection of the components of the natural gas product after individual regeneration of a catalyst of the combustion chamber, based in part on the determined calibration point.

* * * * *